United States Patent
Miyake

(10) Patent No.: US 10,693,079 B2
(45) Date of Patent: *Jun. 23, 2020

(54) MONO AMINE DERIVATIVES AND ORGANIC ELECTROLUMINESCENT DEVICE INCLUDING THE SAME

(71) Applicant: SAMSUNG DISPLAY CO., LTD., Yongin-si, Gyeonggi-do (KR)

(72) Inventor: Hideo Miyake, Yokohama (JP)

(73) Assignee: Samsung Display Co., Ltd., Yongin-si (KR)

(*) Notice: Subject to any disclaimer, the term of this patent is extended or adjusted under 35 U.S.C. 154(b) by 402 days.

This patent is subject to a terminal disclaimer.

(21) Appl. No.: 15/166,151

(22) Filed: May 26, 2016

(65) Prior Publication Data

US 2016/0372677 A1    Dec. 22, 2016

(30) Foreign Application Priority Data

Jun. 17, 2015   (JP) .................................. 2015-121598
Feb. 17, 2016   (JP) .................................. 2016-027794

(51) Int. Cl.
  H01L 51/00    (2006.01)
  C07D 307/91   (2006.01)
  H01L 51/50    (2006.01)

(52) U.S. Cl.
  CPC ........ *H01L 51/0061* (2013.01); *C07D 307/91* (2013.01); *H01L 51/006* (2013.01);
  (Continued)

(58) Field of Classification Search
  CPC .................................................. H01L 51/5056
  See application file for complete search history.

(56) References Cited

U.S. PATENT DOCUMENTS 5,645,948 A   7/1997  Shi et al.
5,935,721 A   8/1999  Shi et al.
(Continued)

FOREIGN PATENT DOCUMENTS

EP   2 364 980 A1   9/2011
EP   2 502 908 A1   9/2012
(Continued)

OTHER PUBLICATIONS

Machine Translation of WO-2013039184-A1.*
(Continued)

*Primary Examiner* — William E McClain
(74) *Attorney, Agent, or Firm* — Lewis Roca Rothgerber Christie LLP

(57) ABSTRACT

A monoamine derivative represented by Formula 1 and an organic electroluminescent device including the same:

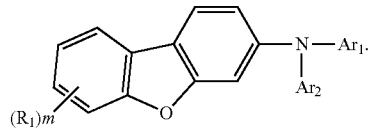

Formula 1

In Formula 1, $Ar_1$ may be represented by Formula 2, $Ar_2$ may be a substituted or unsubstituted aryl group having 6 to 30 carbon atoms for forming a ring, $Ar_1$ and $Ar_2$ may be different from each other, m may be an integer from 0 to 5, $R_1$ may be a substituted or unsubstituted aryl group having 6 to 30 carbon atoms for forming a ring, and when m is 2 or more, a plurality of $R_1$ may combine to form a ring.

(Continued)

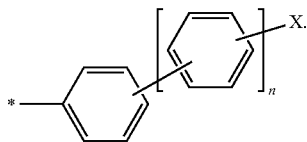

Formula 2

In Formula 2, n may be an integer from 0 to 3; when n is 0, X may be a substituted or unsubstituted aryl group obtained by condensing 2 to 5 benzene rings, and when n is an integer from 1 to 3, X may be naphthyl.

4 Claims, 1 Drawing Sheet

(52) U.S. Cl.
CPC ...... *H01L 51/0058* (2013.01); *H01L 51/0073* (2013.01); *H01L 51/5056* (2013.01)

(56) References Cited

U.S. PATENT DOCUMENTS

| | | | |
|---|---|---|---|
| 6,465,115 B2 | 10/2002 | Shi et al. | |
| 6,596,415 B2 | 7/2003 | Shi et al. | |
| 9,181,474 B2* | 11/2015 | Kim | C07D 213/74 |
| 9,929,355 B2 | 3/2018 | Takada et al. | |
| 10,079,348 B2 | 9/2018 | Jin et al. | |
| 2003/0165715 A1 | 9/2003 | Yoon et al. | |
| 2004/0265630 A1 | 12/2004 | Suh et al. | |
| 2007/0205412 A1 | 9/2007 | Bae et al. | |
| 2010/0044681 A1 | 2/2010 | Kim et al. | |
| 2010/0164371 A1 | 7/2010 | Jeong et al. | |
| 2011/0114930 A1 | 5/2011 | Kim et al. | |
| 2011/0114934 A1 | 5/2011 | Kim et al. | |
| 2012/0074395 A1 | 3/2012 | Yabunouchi et al. | |
| 2012/0146014 A1* | 6/2012 | Kato | C07D 209/86 257/40 |
| 2012/0175600 A1 | 7/2012 | Yabunouchi et al. | |
| 2012/0248426 A1 | 10/2012 | Kato | |
| 2012/0319091 A1 | 12/2012 | Kato | |
| 2013/0200338 A1* | 8/2013 | Kim | C07D 213/74 257/40 |
| 2013/0328021 A1 | 12/2013 | Lim et al. | |
| 2014/0167007 A1 | 6/2014 | Jung et al. | |
| 2014/0197383 A1 | 7/2014 | Cho et al. | |
| 2014/0209875 A1 | 7/2014 | Park et al. | |
| 2015/0228899 A1* | 8/2015 | Kato | C07D 405/14 257/40 |
| 2015/0243891 A1* | 8/2015 | Kato | C07D 333/76 257/40 |
| 2016/0172593 A1* | 6/2016 | Takada | C07D 333/76 257/40 |
| 2016/0372665 A1* | 12/2016 | Takada | H01L 51/006 |
| 2017/0141321 A1* | 5/2017 | Pyo | C07D 307/91 |
| 2017/0317289 A1* | 11/2017 | Lee | C09K 11/06 |
| 2018/0226585 A1* | 8/2018 | Park | C07D 307/91 |

FOREIGN PATENT DOCUMENTS

| | | |
|---|---|---|
| JP | 10-17860 | 1/1998 |
| JP | 11-87067 | 3/1999 |
| JP | 2016-113396 A | 6/2016 |
| JP | 2017-10969 A | 1/2017 |
| JP | 2017-22196 A | 1/2017 |
| KR | 10-0691543 | 3/2007 |
| KR | 10-2007-0104086 | 10/2007 |
| KR | 10-2010-0006979 | 1/2010 |
| KR | 10-2010-0007143 | 1/2010 |
| KR | 10-2010-0071726 | 6/2010 |
| KR | 10-2011-0018195 | 2/2011 |
| KR | 10-2012-0022859 A | 3/2012 |
| KR | 10-2012-0052993 A | 5/2012 |
| KR | 10-2014-0043224 A | 4/2014 |
| KR | 10-1512058 B1 | 4/2015 |
| KR | 10-1516062 B1 | 4/2015 |
| WO | WO 2010/061824 A1 | 6/2010 |
| WO | WO 2010/114017 A1 | 10/2010 |
| WO | WO 2011/021520 A1 | 2/2011 |
| WO | WO 2011/059099 A1 | 5/2011 |
| WO | WO 2011/133007 A2 | 10/2011 |
| WO | WO 2012/091471 A2 | 7/2012 |
| WO | WO-2013039184 A1 * | 3/2013 ........... C07D 333/76 |
| WO | WO-2014088047 A1 * | 6/2014 ........... C07F 7/0809 |
| WO | WO 2015/041492 A1 | 3/2015 |

OTHER PUBLICATIONS

Machine Translation of WO-2014088047-A1.*
Ji et al., Derwent 2015-003897, KR 2014145964, Dec. 24, 2014.
U.S. Office Action dated Sep. 14, 2017, issued in cross-reference U.S. Appl. No. 15/076,581 (6 pages).
U.S. Final Office Action dated Jan. 19, 2018, issued in U.S. Appl. No. 15/076,581, 7 pages.
U.S. Office Action dated Feb. 20, 2015, issued in U.S. Appl. No. 13/598,489 (11 pages).

* cited by examiner

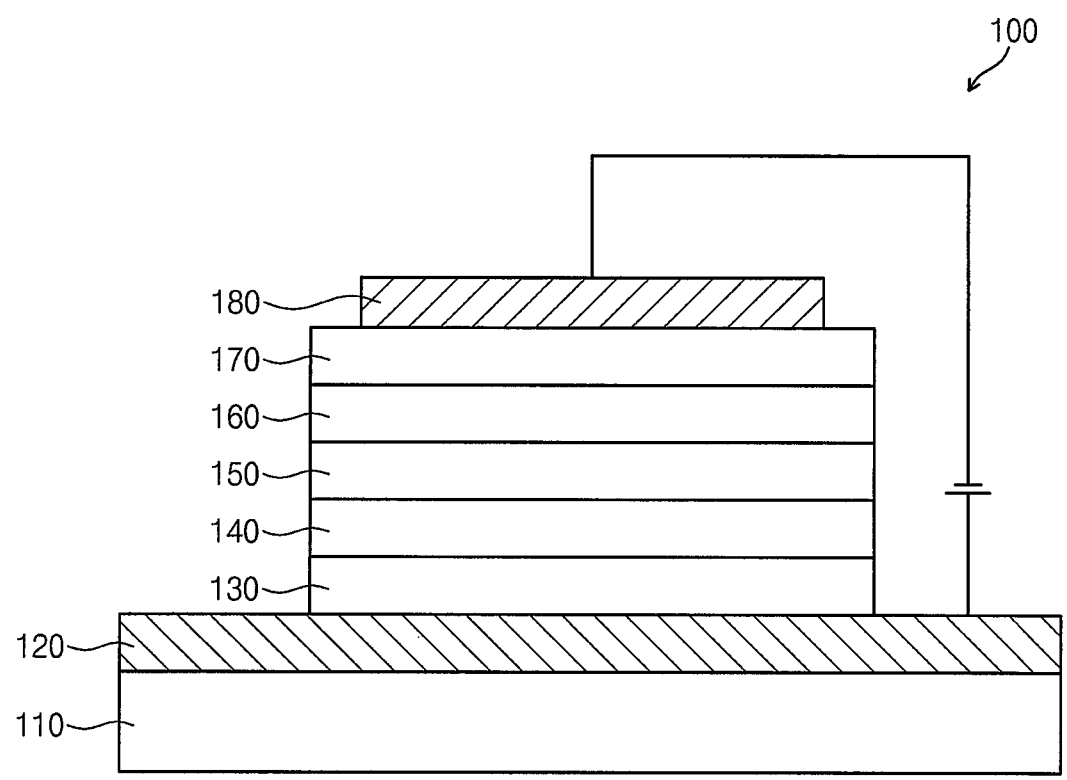

MONO AMINE DERIVATIVES AND ORGANIC ELECTROLUMINESCENT DEVICE INCLUDING THE SAME

CROSS-REFERENCE TO RELATED APPLICATIONS

This application claims priority to and the benefit of Japanese Patent Application Nos. 2015-121598, filed on Jun. 17, 2015, and 2016-027794, filed on Feb. 17, 2016, the entire content of each of which is incorporated herein by reference.

BACKGROUND

One or more aspects of example embodiments of the present disclosure are related to a monoamine derivative and an organic electroluminescent device including the same.

Recently, developments have been actively conducted on display devices and lighting installations using organic electroluminescent (EL) devices, which are self-luminescent light-emitting devices. An organic EL device with high performance characteristics is required for use in display devices and lighting installations.

An example organic EL device has a laminated structure including an anode, a hole injection layer, a hole transfer layer, an emission layer, an electron transfer layer, an electron injection layer, and a cathode, stacked in this stated order. In the organic EL device having such a structure, holes and electrons injected from the anode and the cathode, respectively, may recombine to produce excitons in the emission layer, and light emission may be attained via the transition (e.g., radiative decay) of the excitons from an excited state to the ground state.

In order to improve the performance of the organic EL device, it is important to improve the performance of the materials in each layer. For example, various aromatic amine compounds are known in the related art as hole transfer materials for an organic EL device.

SUMMARY

However, the emission properties of such aromatic compounds in organic EL devices of the related art are still insufficient.

One or more aspects of example embodiments of the present disclosure are directed toward a novel monoamine derivative that is capable of further improving the emission efficiency of an organic EL device, and an organic EL device including the monoamine derivative.

One or more example embodiments of the present disclosure provide a monoamine amine derivative represented by Formula 1:

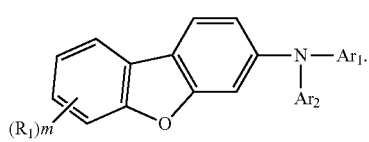

Formula 1

In Formula 1, $Ar_1$ may be represented by Formula 2, $Ar_2$ may be a substituted or unsubstituted aryl group having 6 to 30 carbon atoms for forming a ring, $Ar_1$ and $Ar_2$ may be different from each other, m may be an integer from 0 to 5, $R_1$ may be a substituted or unsubstituted aryl group having 6 to 30 carbon atoms for forming a ring, and when m is 2 or more, a plurality of $R_1$ may combine (e.g., couple) to form a ring.

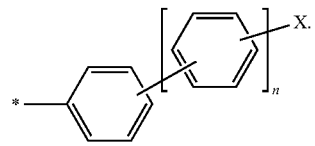

Formula 2

In Formula 2, n may be an integer from 0 to 3, when n is 0, X may be a substituted or unsubstituted aryl group obtained by condensing (e.g., fusing) 2 to 5 benzene rings, and when n is an integer from 1 to 3, X may be a naphthyl group.

With respect to the above, the emission efficiency of an organic EL device may be further improved by the monoamine derivative represented by Formula 1.

In some embodiments, m may be 0.

With respect to the above, the emission efficiency of an organic EL device may be further improved by the monoamine derivative represented by Formula 1.

In some embodiments, n may be 0, and X may be represented by one selected from the following groups:

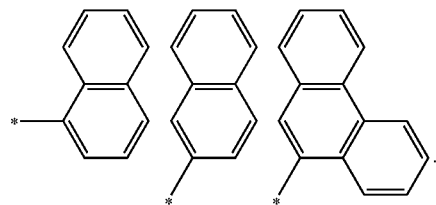

With respect to the above, the emission efficiency of an organic EL device may be further improved by the monoamine derivative represented by Formula 1.

In some embodiments, n may be 0, and $Ar_2$ may be a substituted or unsubstituted aryl group having 6 to 14 carbon atoms for forming a ring.

With respect to the above, the emission efficiency of an organic EL device may be further improved by the monoamine derivative represented by Formula 1.

In some embodiments, n may be an integer from 1 to 3, and X may be represented by Formula 3:

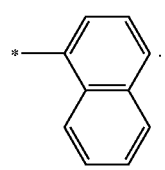

Formula 3

With respect to the above, the emission efficiency of an organic EL device may be further improved by the monoamine derivative represented by Formula 1.

In some embodiments, the monoamine derivative represented by Formula 1 may be represented by Formula 4:

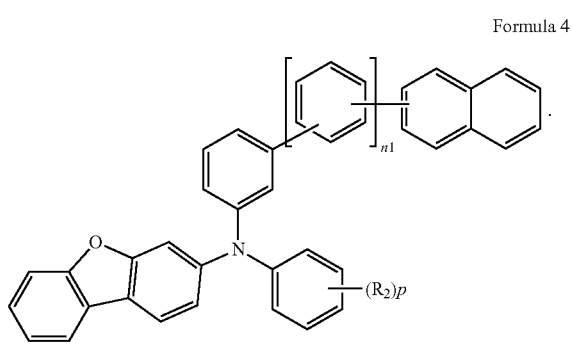

Formula 4

In Formula 4, n1 may be an integer from 1 to 3, p may be an integer from 1 to 5, $R_2$ may be a substituted or unsubstituted aryl group having 6 to 30 carbon atoms for forming a ring, and when p is 2 or more, a plurality of $R_2$ may combine (e.g., couple) to form a ring.

With respect to the above, the emission efficiency of an organic EL device may be further improved by the monoamine derivative represented by Formula 1.

In some embodiments, n may be an integer from 1 to 3, and $Ar_2$ may be a substituted or unsubstituted aryl group having 6 to 18 carbon atoms for forming a ring.

With respect to the above, the emission efficiency of an organic EL device may be further improved by the monoamine derivative represented by Formula 1.

One or more embodiments of the present disclosure provide an organic EL device including the monoamine derivative according to an embodiment of the present disclosure in at least one layer.

An organic EL device according to an embodiment of the present disclosure includes a first electrode, a second electrode on the first electrode, and at least one organic layer between the first electrode and the second electrode, wherein the at least one organic layer includes the monoamine derivative represented by Formula 1.

With respect to the above, an organic EL device having a further improved emission efficiency may be provided.

In some embodiments, the organic EL device may include an emission layer between the first electrode and the second electrode, and the monoamine derivative in at least one layer between the first electrode and the emission layer.

With respect to the above, an organic EL device having a further improved emission efficiency may be provided.

In some embodiments, the organic layer including the monoamine derivative may be at least one selected from a hole injection layer or a hole transfer layer.

With respect to the above, an organic EL device having a further improved emission efficiency may be provided.

BRIEF DESCRIPTION OF THE DRAWING

The accompanying drawing is included to enable further understanding of the present disclosure, and is incorporated in and constitutes a part of this specification. The drawing illustrates example embodiments of the present disclosure and, together with the description, serves to explain principles of the present disclosure. In the drawing:

The drawing is a schematic diagram illustrating the structure of an organic EL device according to an embodiment of the present disclosure.

DETAILED DESCRIPTION

Hereinafter, example embodiments of the present disclosure will be described in more detail with reference to the accompanying drawing. The monoamine derivative according to an embodiment of the present disclosure and the organic electroluminescent device including the monoamine derivative may, however, be embodied in different forms and should not be construed as being limited to the example embodiments set forth herein. In the drawing, elements having substantially the same function will be designated by the same reference numerals, and repeated explanations thereof may not be provided.

In the drawings, the thicknesses of layers, films, panels, regions, etc., may be exaggerated for clarity. It will be understood that when an element such as a layer, film, region, or substrate is referred to as being "on" another element, it can be directly on the other element or intervening element(s) may also be present. In contrast, when an element is referred to as being "directly on" another element, no intervening elements are present.

1. Monoamine Derivative

First, a monoamine derivative according to an embodiment of the present disclosure will be explained. The monoamine derivative according to an embodiment of the present disclosure is a compound represented by Formula 1, which may be used as a material for an organic EL device:

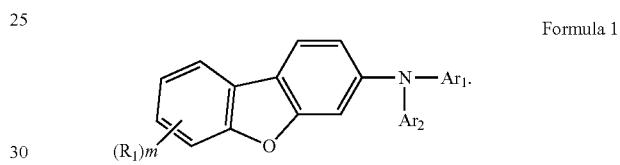

Formula 1

In Formula 1, $Ar_1$ may be represented by Formula 2, $Ar_2$ may be a substituted or unsubstituted aryl group having 6 to 30 carbon atoms for forming a ring, $Ar_1$ and $Ar_2$ may be different from each other, m may be an integer from 0 to 5, and $R_1$ may be a substituted or unsubstituted aryl group having 6 to 30 carbon atoms for forming a ring, and when m is 2 or more, a plurality of $R_1$ may combine (e.g., couple) to form a ring. As used herein, "atoms for forming a ring" may refer to "ring-forming atoms".

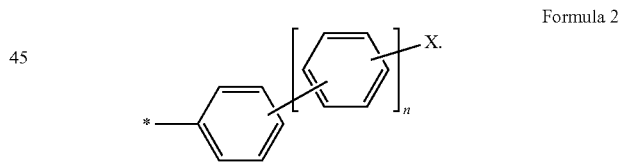

Formula 2

In Formula 2, n may be an integer from 0 to 3. When n is 0, X may be a substituted or unsubstituted aryl group obtained by condensing (e.g., fusing) 2 to 5 benzene rings, and when n is an integer from 1 to 3, X may be a naphthyl group.

The monoamine derivative represented by Formula 1 according to an embodiment of the present disclosure may be characterized (e.g., described) as a molecule with an amine group directly substituted at position 3 of dibenzofuran.

In the present disclosure, * refers to a connecting part (e.g., binding site) with another substituent.

In some embodiments, m may be 0. For example, the dibenzofuran that forms the core structure may be unsubstituted. However, embodiments of the present disclosure are not limited thereto, and for example, m may be 1, and $R_1$ may be phenyl.

When n is 0, X may be an aryl group obtained by condensing (e.g., fusing) 2 to 5 benzene rings, the phenylene ring and substituent X may be sterically twisted (e.g., oriented on perpendicular planes with respect to each other, due to steric hindrance), and the conjugation of electrons (e.g., electron conjugation) may be blocked or reduced between the phenylene ring and the substituent X. Accordingly, the highest occupied molecular orbital (HOMO) energy level of the monoamine derivative according to an embodiment of the present disclosure may become deeper or more stabilized (e.g., the absolute value of the HOMO energy level may increase). Therefore, when the monoamine derivative according to an embodiment of the present disclosure is used as a hole transfer material, the energy gap between the hole transfer layer and the emission layer may decrease. Accordingly, the transfer of holes from the hole transfer layer to the emission layer may become easy (e.g., more facile) in the monoamine derivative according to an embodiment of the present disclosure, and the emission efficiency of the organic EL device may be further improved or increased.

In some embodiments, when n is 0, X may be represented by one of the following groups. When X is represented by one of the following groups, the monoamine derivative according to an embodiment of the present disclosure may further improve the emission efficiency of the organic EL device:

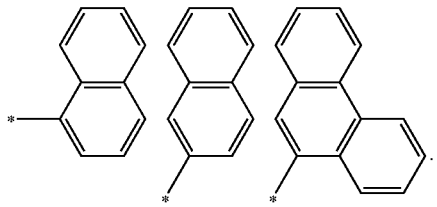

$Ar_2$ may be different from $Ar_1$, as described above, and may be a substituted or unsubstituted aryl group having 6 to 30 carbon atoms for forming a ring. For example, $Ar_2$ may be a phenyl group, a biphenyl group, a terphenyl group, a naphthyl group, an anthryl group, a phenanthrenyl group, a fluorenyl group, an indenyl group, a pyrenyl group, a fluoranthenyl group, or a triphenylenyl group.

When n is 0, $Ar_2$ may be a substituted or unsubstituted aryl group having 6 to 14 carbon atoms for forming a ring. For example, $Ar_2$ may be a phenyl group, a biphenyl group, a terphenyl group, a naphthyl group, a phenanthrenyl group, or a fluorenyl group. When $Ar_2$ is a substituent having a large molecular weight (e.g., $Ar_2$ may have 15 or more carbon atoms), the thermotolerance of the monoamine derivative according to an embodiment of the present disclosure may be deteriorated or decreased, and layer formation by a deposition process may become difficult.

When the fluorenyl group is substituted, groups

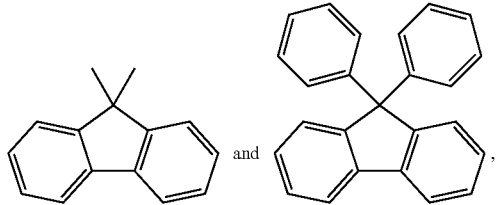

etc. may be included, without limitation.

In some embodiments, the substituents for $Ar_2$ in Formula 1 and X in Formula 2 may each not include an amino group in the structure thereof. For example, the compound represented by Formula 1 according to an embodiment of the present disclosure may be a monoamine derivative having only one amino group in the structure thereof. Non-limiting examples of the substituent for $Ar_2$ in Formula 1 and X in Formula 2 may include an alkyl group, an alkenyl group, an alkynyl group, a halogen atom, a hydroxyl group, a cyano group, a nitro group, an alkoxy group, an aryloxy group, an aryl group, a heteroaryl group, etc.

When n is 0, the monoamine derivative represented by Formula 1 may be represented by at least one selected from Compounds 1 to 18. However, the monoamine derivative according to an embodiment of the present disclosure is not limited to Compounds 1 to 18:

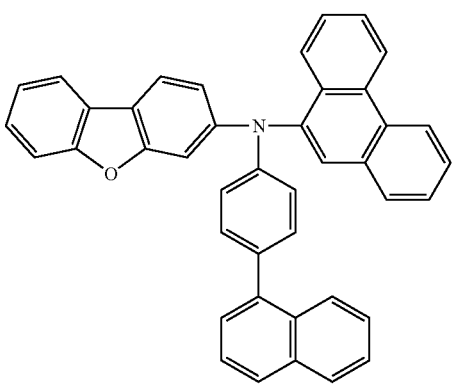

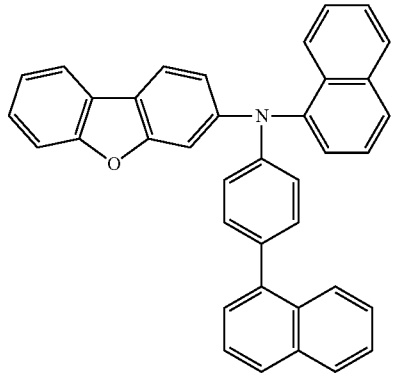

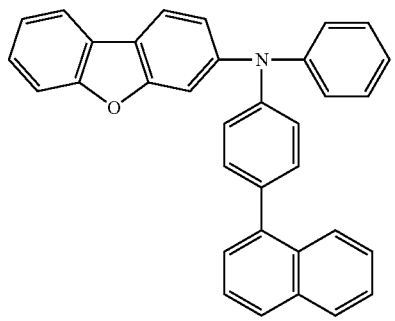

4
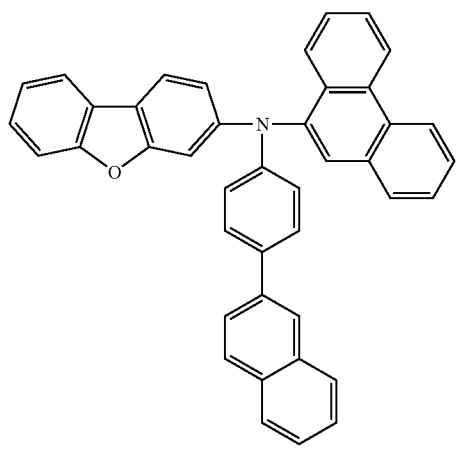
5
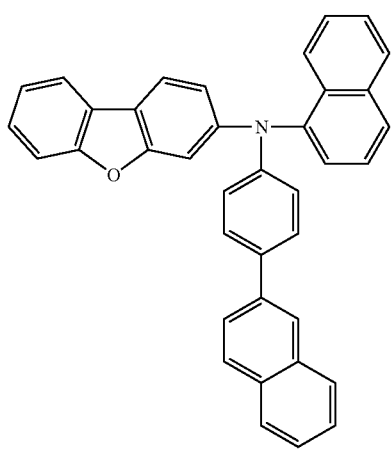
6
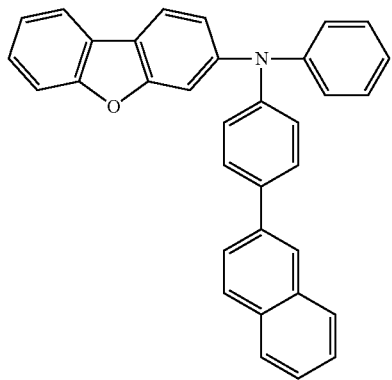
7
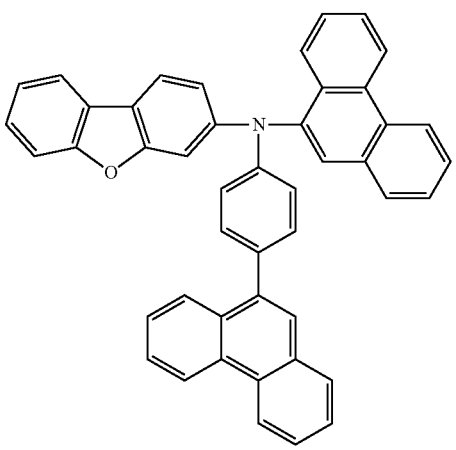
8
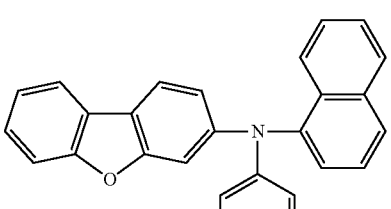
9
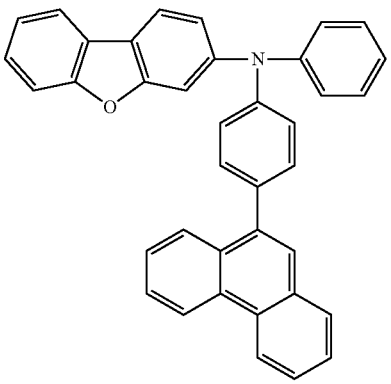
10
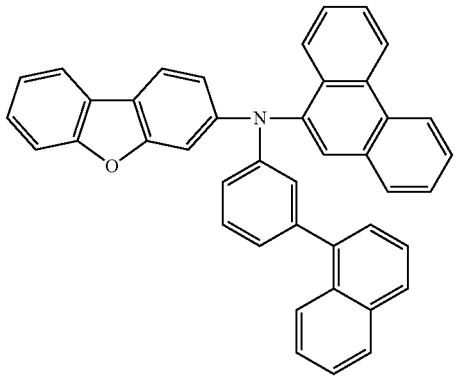

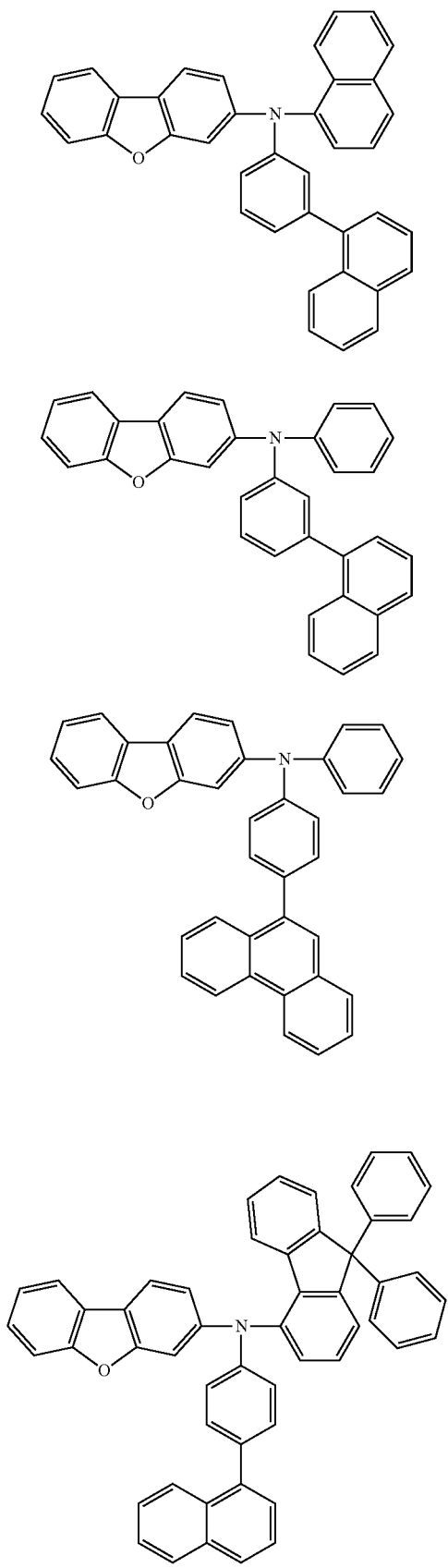
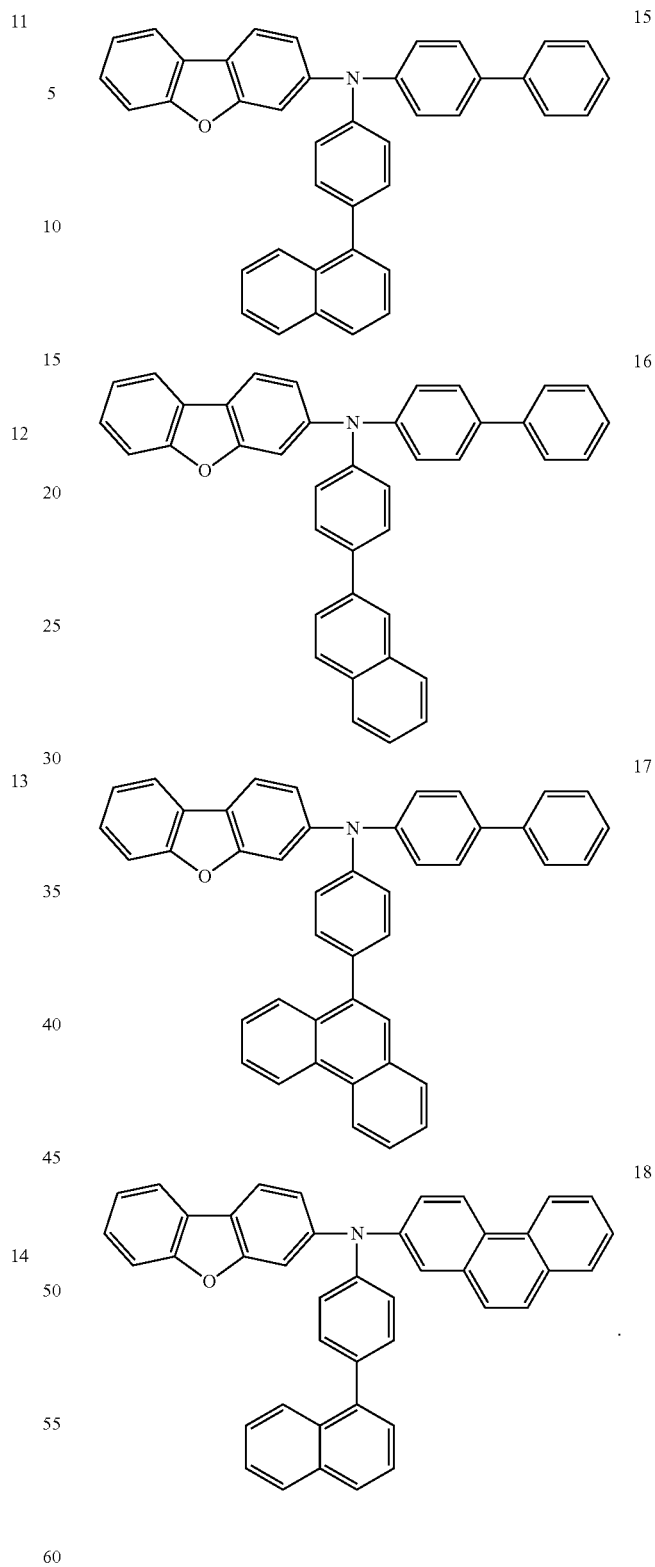
As described above, when n is an integer from 1 to 3, X may be a naphthyl group. For example, when n is an integer from 1 to 3, X may be represented by Formula 3:

Formula 3

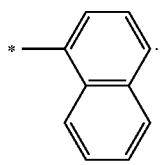

In some embodiments, the monoamine derivative represented by Formula 1 may be represented by Formula 4:

Formula 4

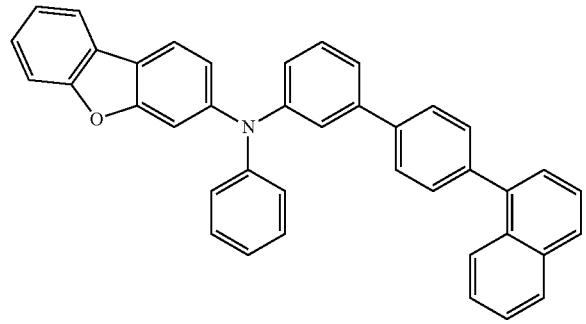

In Formula 4, n1 may be an integer from 1 to 3, p may be an integer from 1 to 5, $R_2$ may be a substituted or unsubstituted aryl group having 6 to 30 carbon atoms for forming a ring, and when p is 2 or more, a plurality of $R_2$ may combine (e.g., couple) to form a ring.

The monoamine derivative represented by Formula 4 corresponds to (e.g., describes) a case in which a phenylene group that is directly linked to an amine group is substituted with a second group at a meta position. The emission efficiency of an organic EL device may be further improved by using the monoamine derivative represented by Formula 4. As used herein, the term "directly linked" may refer to "connected by a bond such as a single bond".

When n is an integer from 1 to 3, $Ar_2$ may be a substituted or unsubstituted aryl group having 6 to 18 carbon atoms for forming a ring.

When n is an integer from 1 to 3, the monoamine derivative represented by Formula 1 may be represented by at least one selected from Compounds 19 to 41. However, the monoamine derivative according to an embodiment of the present disclosure is not limited to Compounds 19 to 41:

19

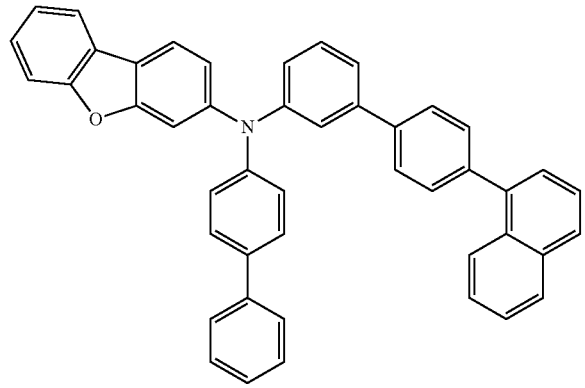

20

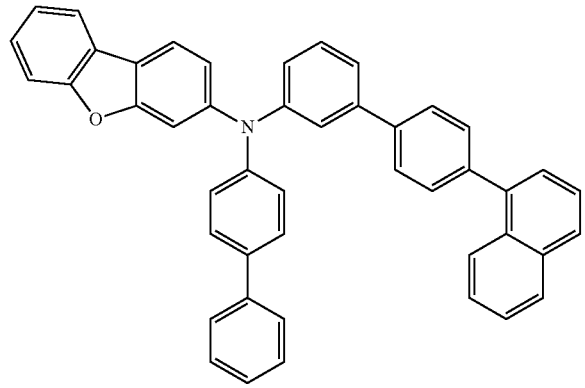

21

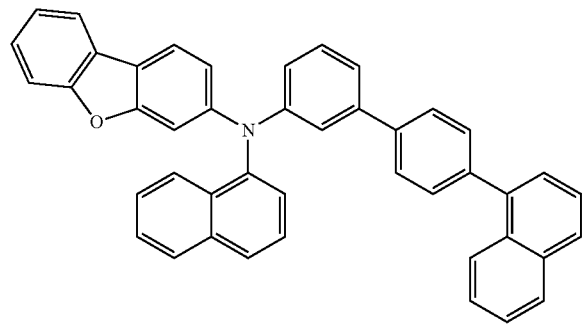

22

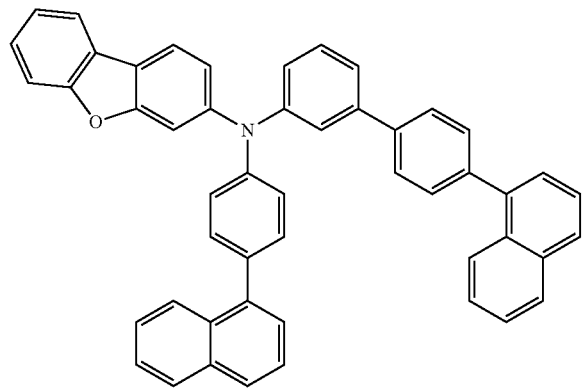

-continued
23
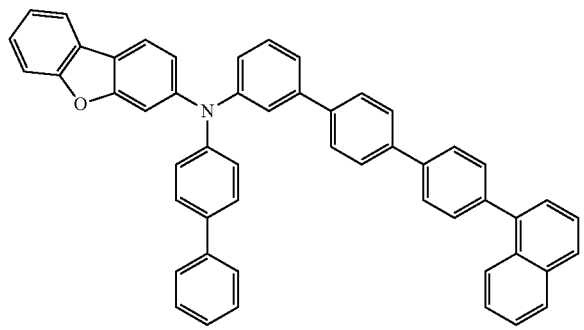
24
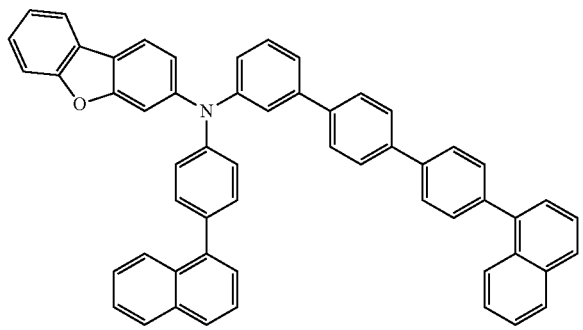
25
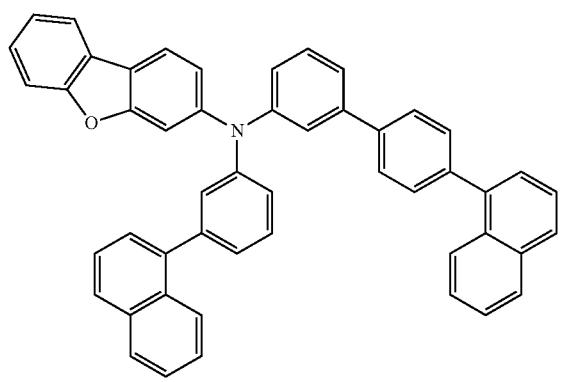
26
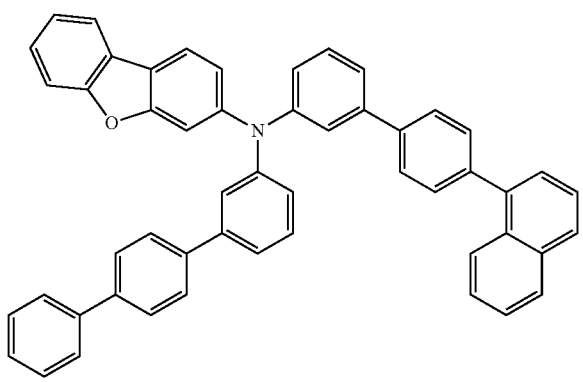
27
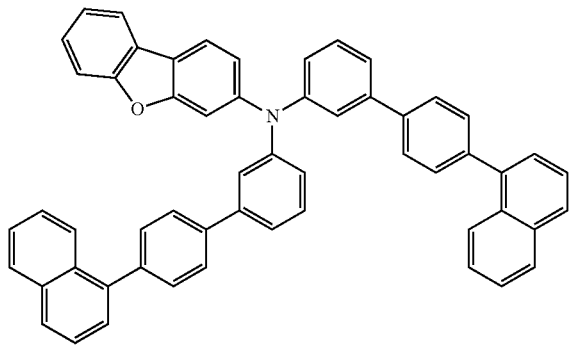
28
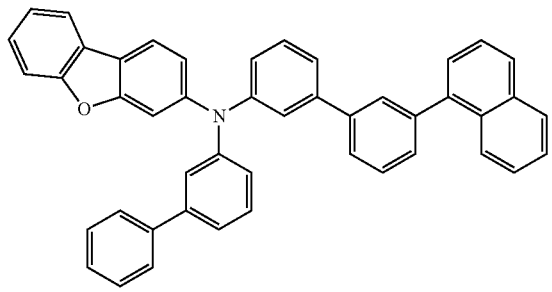
29
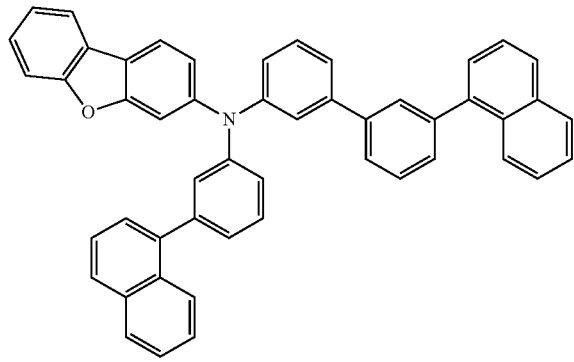
30
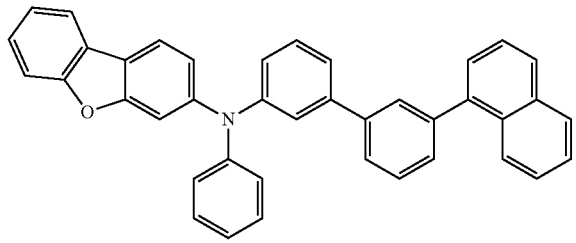

-continued
31
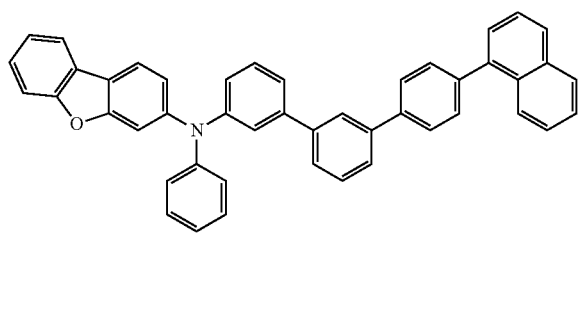
32
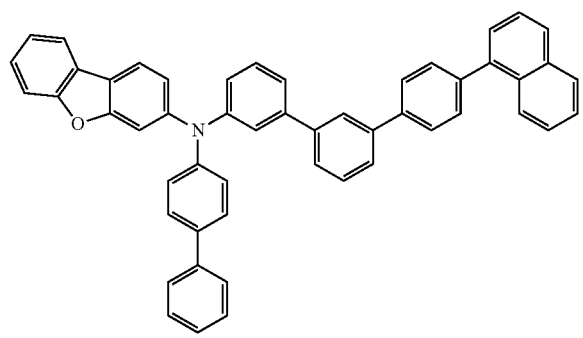
33
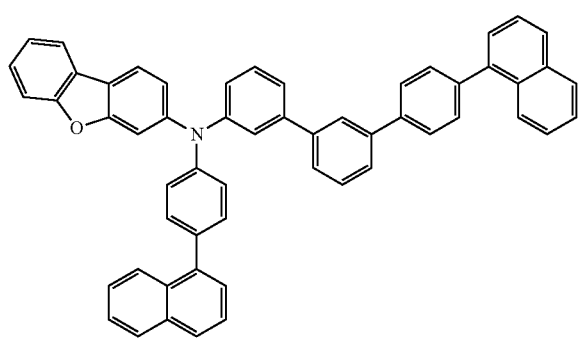
34
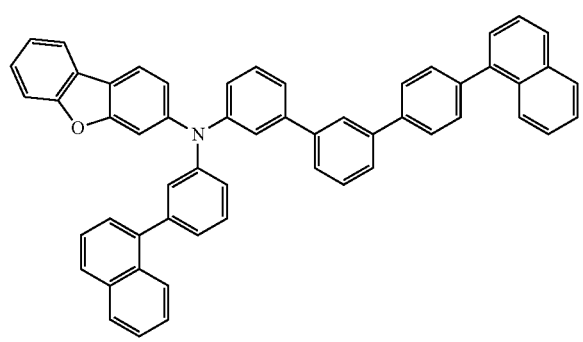
35
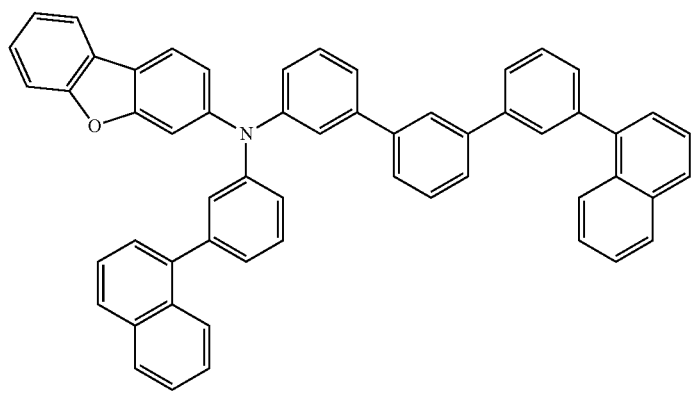
36
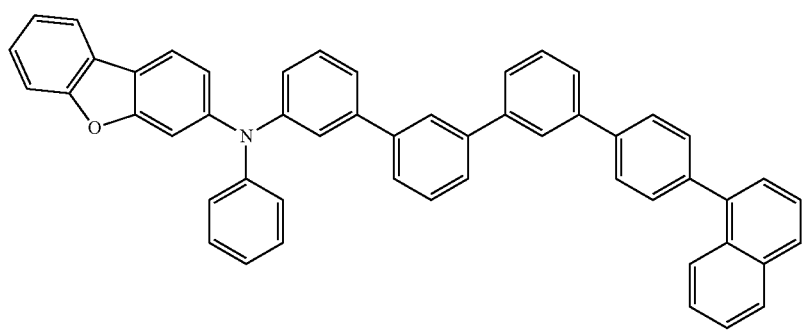

-continued

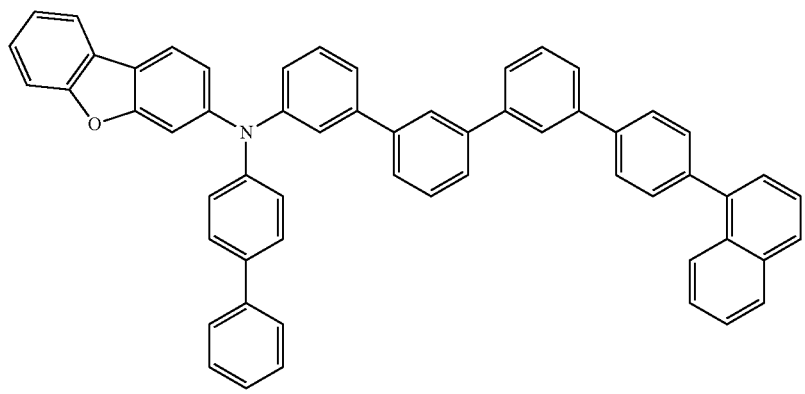

37

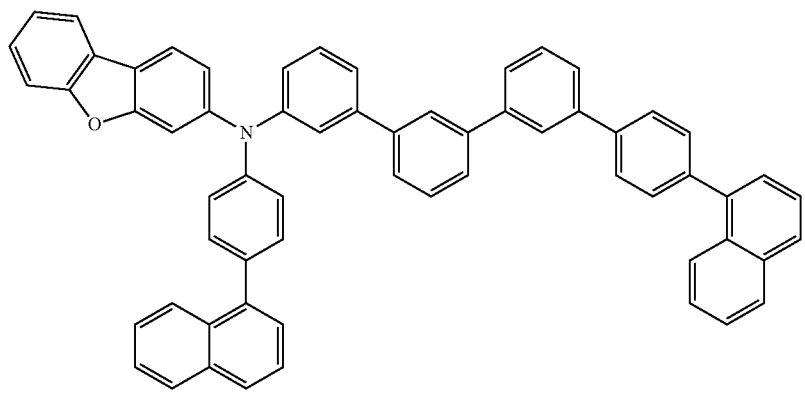

38

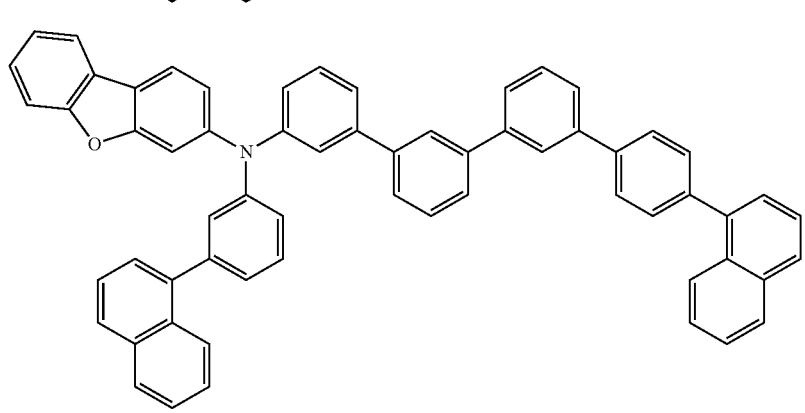

39

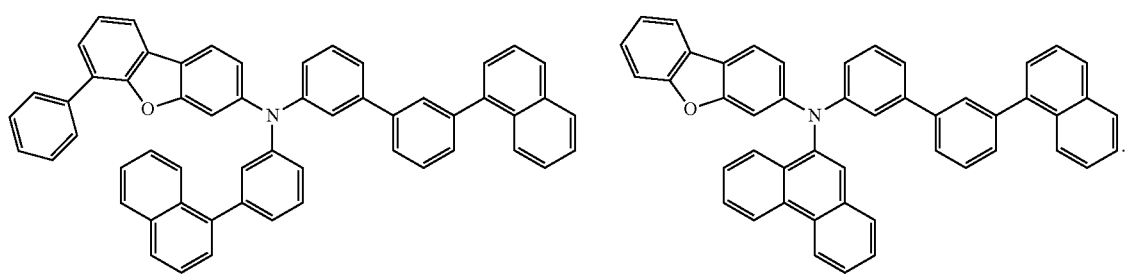

40 41

The emission efficiency of the organic EL device may be further improved by including the monoamine derivative according to an embodiment of the present disclosure in at least one layer of the organic EL device.

In some embodiments, the monoamine derivative according to an embodiment of the present disclosure may be included in at least one layer between an emission layer and an anode in the organic EL device.

For example, the monoamine derivative according to an embodiment of the present disclosure may be included in at least one selected from a hole transfer layer and a hole injection layer in the organic EL device.

When the monoamine derivative according to an embodiment of the present disclosure has a deep (e.g., low) HOMO energy level, the energy gap between the layer including the monoamine derivative according to an embodiment of the present disclosure and the emission layer may decrease, thereby improving the hole transfer efficiency of the device. Accordingly, the monoamine derivative according to an embodiment of the present disclosure may enable a further increase in the emission efficiency of the organic EL device.

However, in the organic EL device, the layer including the monoamine derivative according to an embodiment of the present disclosure is not limited to the above-mentioned layers. For example, the monoamine derivative according to an embodiment of the present disclosure may be included in at least one selected from the organic layers between the anode and the cathode in the organic EL device.

In some embodiments, the monoamine derivative according to an embodiment of the present disclosure may be used in an organic EL device including an emission layer including a luminescent material with blue to bluish green color. When the monoamine derivative according to an embodiment of the present disclosure is used in such an organic EL device, the emission efficiency of the organic EL device may be further improved.

As described above, the monoamine derivative according to an embodiment of the present disclosure may further improve the emission efficiency of the organic EL device. The monoamine derivative according to an embodiment of the present disclosure may be used as the hole transfer material of an organic EL device, and in some embodiments, may be used as the hole transfer material of an organic EL device including an emission layer including a luminescent material with blue to bluish green color.

Thus far, the monoamine derivative according to an embodiment of the present disclosure has been explained in detail.

2. Organic EL Device

Hereinafter, an organic EL device including the amine derivative according to an embodiment of the present disclosure will be described in more detail with reference to the drawing. The drawing is a schematic diagram of an organic EL device according to an embodiment of the present disclosure.

As shown in the drawing, an organic EL device 100 according to an embodiment of the present disclosure includes a substrate 110, a first electrode 120 on the substrate 110, a hole injection layer 130 on the first electrode 120, a hole transfer layer 140 on the hole injection layer 130, an emission layer 150 on the hole transfer layer 140, an electron transfer layer 160 on the emission layer 150, an electron injection layer 170 on the electron transfer layer 160, and a second electrode 180 on the electron injection layer 170.

The organic EL device 100 according to an embodiment of the present disclosure includes the first electrode 120, the second electrode 180 on the first electrode 120, and at least one organic layer between the first electrode 120 and the second electrode 180, wherein the at least one organic layer includes the monoamine derivative according to an embodiment of the present disclosure.

In one embodiment, the organic EL device 100 according to an embodiment of the present disclosure includes an emission layer 150 between the first electrode 120 and the second electrode 180, and the monoamine derivative according to an embodiment of the present disclosure may be included in at least one layer between the first electrode 120 and the emission layer 150.

In this case, the monoamine derivative according to an embodiment of the present disclosure may be included in at least one selected from the hole injection layer 130 and the hole transfer layer 140 positioned between the first electrode 120 and the emission layer 150.

The substrate 110 may be any suitable substrate used in organic EL devices in the related art. For example, the substrate 110 may be a glass substrate, a semiconductor substrate (such as a silicon substrate, etc.), or a transparent plastic substrate.

The first electrode 120 may be on the substrate 110. For example, the first electrode 120 may be an anode and may include a material having a large work function (such as a metal, an alloy, and/or a conductive compound). For example, the first electrode 120 may be a transmission type (e.g., transmissive) electrode including indium tin oxide ($In_2O_3$—$SnO_2$:ITO), indium zinc oxide ($In_2O_3$—ZnO), tin oxide ($SnO_2$), zinc oxide (ZnO), etc., each having good transparency and/or conductivity. In some embodiments, the first electrode 120 may be a reflection type (e.g., reflective) electrode including magnesium (Mg), aluminum (Al), etc. laminated on or above a transparent conductive layer.

The hole injection layer 130 may be on the first electrode 120. The hole injection layer 130 may facilitate easy injection of holes from the first electrode 120, and may have a thickness of, for example, about 10 nm to about 150 nm.

The hole injection layer 130 may include the monoamine derivative according to an embodiment of the present disclosure, and may include any suitable hole injection material available in the related art. The hole injection material included in the hole injection layer 130 may include, for example, a triphenylamine-containing poly(ether ketone) (TPAPEK), 4-isopropyl-4'-methyldiphenyliodonium tetrakis(pentafluorophenyl)borate (PPBI), N,N'-diphenyl-N,N'-bis-[4-(phenyl-m-tolyl-amino)-phenyl]-biphenyl-4,4'-diamine (DNTPD), copper phthalocyanine, 4,4',4''-tris(3-methylphenylphenylamino)triphenylamine (m-MTDATA), N,N'-di(1-naphthyl)-N,N'-diphenylbenzidine (NPB), 4,4',4''-tris{diphenylamino}triphenylamine (TDATA), 4,4',4''-tris(N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate) (PEDOT/PSS), polyaniline/10-camphor sulfonic acid (PANI/CSA), etc.

The hole transfer layer 140 may be on the hole injection layer 130. The hole transfer layer 140 may facilitate the transfer of holes, and may have a thickness of about 10 nm to about 150 nm. In some embodiments, the hole transfer layer 140 may be provided in plural.

In some embodiments, the hole transfer layer 140 may include the monoamine derivative according to an embodiment of the present disclosure. In some embodiments, in the case where the monoamine derivative according to an embodiment of the present disclosure is included in another layer (for example, the hole injection layer 130, etc.), the hole transfer layer 140 may include any suitable hole transfer material. The hole transfer material may include, for example, 1,1-bis[(di-4-tolylamino)phenyl]cyclohexane (TAPC), a carbazole derivative (such as N-phenylcarbazole and/or polyvinylcarbazole), N,N'-bis(3-methylphenyl)-N,N'-diphenyl-[1,1-biphenyl]-4,4'-diamine (TPD), 4,4',4''-tris(N-carbazolyl)triphenylamine (TCTA), N,N'-di(1-naphthyl)-N,N'-diphenylbenzidine (NPB), etc.

The emission layer 150 may be on the hole transfer layer 140. The emission layer 150 may emit light by fluorescence, phosphorescence, etc. and may have a thickness of about 10 nm to about 60 nm. As the luminescent material of the emission layer 150, any suitable luminescent material may be used. For example, luminescent materials including a fluoranthene derivative, a styrene derivative, a pyrene derivative, an arylacetylene derivative, a fluorene derivative, a perylene derivative, a chrysene derivative, an anthracene derivative, etc. may be used. In some embodiments, as the luminescent material of the emission layer 150, the styrene derivative, the pyrene derivative, the perylene derivative, or the anthracene derivative may be used.

In some embodiments, as the luminescent material of the emission layer 150, an anthracene derivative represented by Formula 5 may be used:

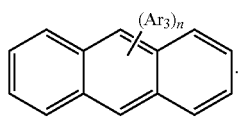

Formula 5

In Formula 5, each $Ar_3$ may independently be a hydrogen atom, a deuterium atom, a substituted or unsubstituted alkyl group having 1 to 50 carbon atoms, a substituted or unsubstituted cycloalkyl group having 3 to 50 carbon atoms for forming a ring, a substituted or unsubstituted alkoxy group having 1 to 50 carbon atoms, a substituted or unsubstituted aralkyl group having 7 to 50 carbon atoms, a substituted or unsubstituted aryloxy group having 6 to 50 carbon atoms for forming a ring, a substituted or unsubstituted arylthio group having 6 to 50 carbon atoms for forming a ring, a substituted or unsubstituted alkoxycarbonyl group having 2 to 50 carbon atoms, a substituted or unsubstituted aryl group having 6 to 50 carbon atoms for forming a ring, a substituted or unsubstituted heteroaryl group having 5 to 50 carbon atoms for forming a ring, a substituted or unsubstituted silyl group, a carboxyl group, a halogen atom, a cyano group, a nitro group, or a hydroxyl group, and n may be an integer from 1 to 10.

For example, each $Ar_3$ may independently be a phenyl group, a biphenyl group, a terphenyl group, a naphthyl group, a phenylnaphthyl group, a naphthylphenyl group, an anthryl group, a phenanthryl group, a fluorenyl group, an indenyl group, a pyrenyl group, an acenaphthenyl group, a fluoranthenyl group, a triphenylenyl group, a pyridyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, etc.

In some embodiments, each $Ar_3$ may independently be a phenyl group, a biphenyl group, a terphenyl group, a naphthyl group, a phenylnaphthyl group, a naphthylphenyl group, a phenanthryl group, a fluorenyl group, a carbazolyl group, a dibenzofuranyl group, a dibenzothienyl group, etc.

The compound represented by Formula 5 may be represented by, for example, at least one selected from Compounds a-1 to a-12. However, embodiments of the compound represented by Formula 5 are not limited to Compounds a-1 to a-12:

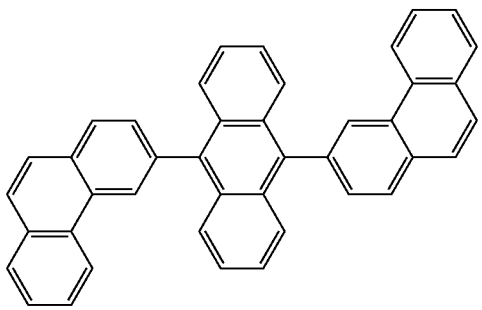

a-1

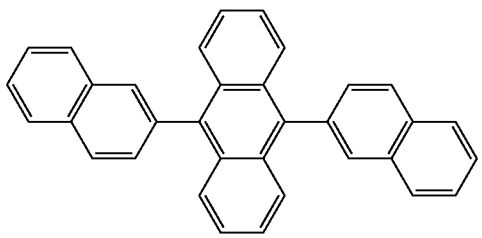

a-2

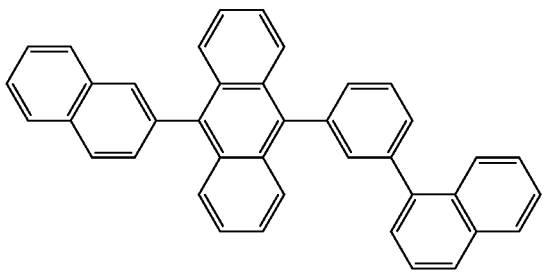

a-3

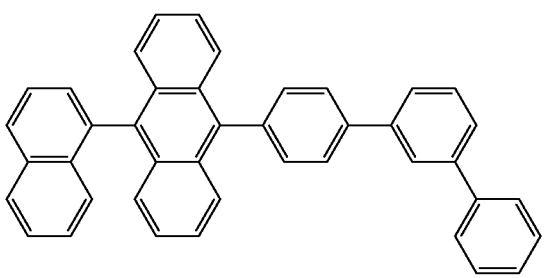

a-4

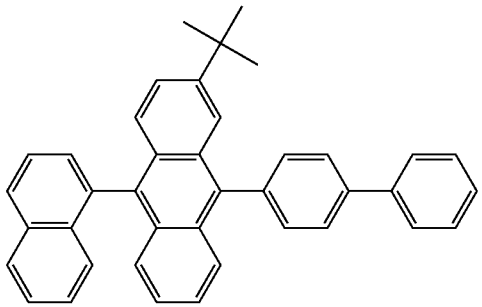

a-5

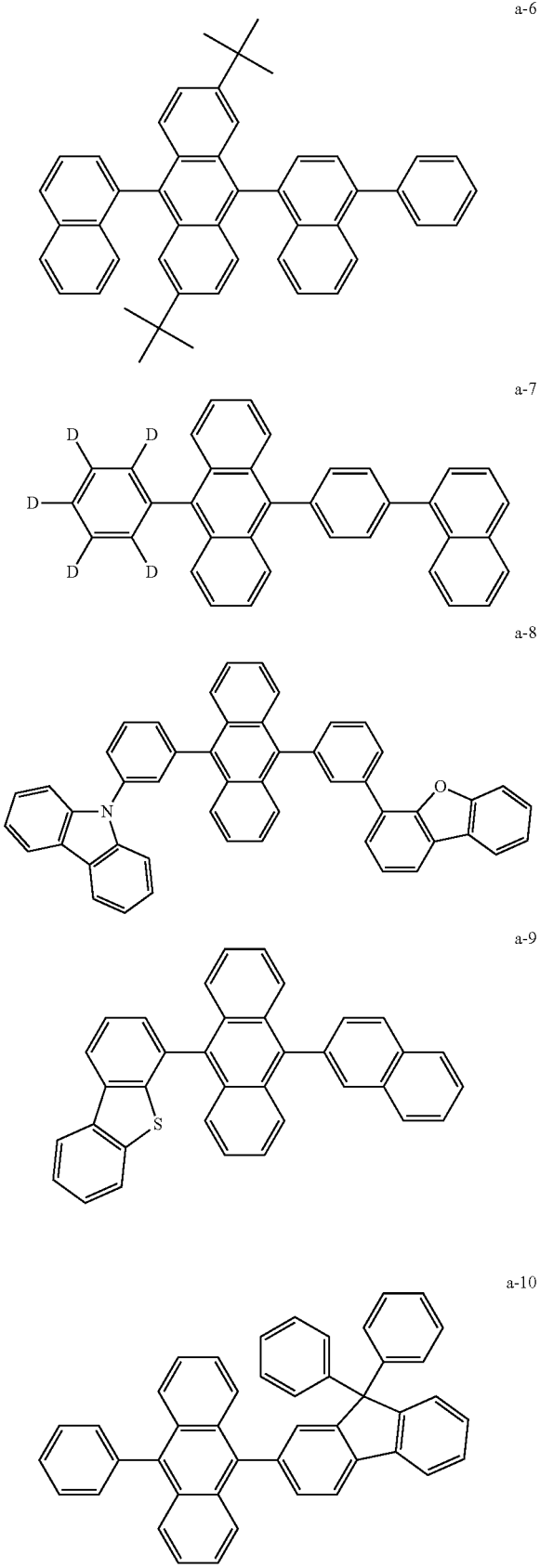
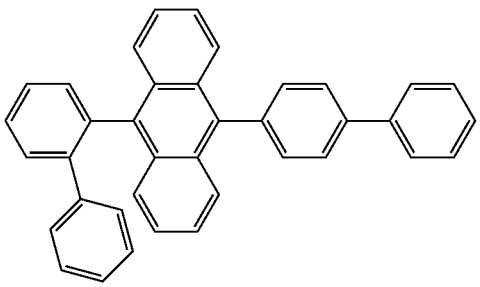
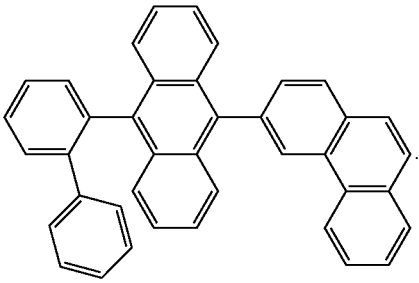

In some embodiments, in the emission layer 150, a styrene derivative (such as 1,4-bis[2-(3-N-ethylcarbazolyl)vinyl]benzene (BCzVB), 4-(di-p-tolylamino)-4'-[(di-p-tolylamino)styryl]stilbene (DPAVB), and/or N-(4-((E)-2(6-((E)-4-(diphenylamino)styryl)naphthalene-2-yl)vinyl)phenyl)-N-phenylbenzeneamine (N-BDAVBi)) may be used as the luminescent material. In some embodiments, in the emission layer 150, a perylene derivative (such as 2,5,8,11-tetra-t-butylperylene (TBPe)) may be used, and a pyrene derivative (such as 1,1-dipyrene, 1,4-dipyrenylbenzene and/or 1,4-bis(N,N-diphenylamino)pyrene) may be used as the luminescent material. However, embodiments of the luminescent material included in the emission layer 150 of the organic EL device 150 according to an embodiment of the present disclosure are not limited thereto.

The electron transfer layer 160 may be on the emission layer 150. The electron transfer layer 160 may have electron transferring function and may have a thickness of about 15 nm to about 50 nm.

The electron transfer layer 160 may include any suitable electron transfer material. The electron transfer material may include, for example, tris(8-quinolinolato)aluminum (Alq$_3$), a material having a nitrogen-containing aromatic ring, etc. Non-limiting examples of the nitrogen-containing aromatic ring may include a material including a pyridine ring (such as 1,3,5-tri[(3-pyridyl)-phen-3-yl]benzene), a material including a triazine ring (such as 2,4,6-tris(3'-(pyridin-3-yl)biphenyl-3-yl)-1,3,5-triazine), a material including an imidazole ring (such as 2-(4-(N-phenylbenzoimidazolyl-1-yl-phenyl)-9,10-dinaphthylanthracene)), etc.

The electron injection layer 170 may be on the electron transfer layer 160. The electron injection layer 170 may enable easy injection of electrons from the second electrode 180 and may have a thickness of about 0.3 nm to about 9 nm. The electron injection layer 170 may include any suitable material available in the related art. For example, the electron injection layer 170 may include (8-quinolinato)lithium (LiQ), a lithium compound (such as lithium fluoride (LiF) and/or lithium oxide (Li$_2$O)), sodium chloride (NaCl), cesium fluoride (CsF), barium oxide (BaO), etc.

The second electrode 180 may be on the electron injection layer 170. The second electrode 180 may be, for example, a cathode and may be a reflection type (e.g., reflective) electrode using a metal, an alloy, a conductive compound, etc., each having a small work function. For example, the second electrode 180 may include a metal (such as lithium (Li), magnesium (Mg), aluminum (Al), and/or calcium (Ca)), or an alloy (such as aluminum-lithium (Al—Li), magnesium-indium (Mg—In), magnesium-silver (Mg—Ag), etc.). In some embodiments, the second electrode 180 may be formed as a transmission type electrode using a thin film of the metal material with a thickness of about 20 nm or less, or may be formed as a transparent conductive layer (such as indium tin oxide ($In_2O_3$—$SnO_2$), indium zinc oxide ($In_2O_3$—ZnO), etc.).

In some embodiments, each layer described above may be formed by selecting an appropriate layer forming method according to the materials to be used (such as vacuum deposition, sputtering, and/or one or more coating methods according to the material to be used in each layer). For example, one or more metal layers (such as the first electrode 120, the electron injection layer 170, and/or the second electrode 180) may be formed using the vacuum deposition method, the sputtering method, etc. In some embodiments, one or more organic layers between the first electrode 120 and the second electrode 180 may be formed using a vacuum deposition method, a coating method, etc.

The organic EL device 100 according to an embodiment of the present disclosure has been explained. The organic EL device 100 according to an embodiment of the present disclosure may attain further improved emission efficiency by including the monoamine derivative represented by Formula 1.

The configuration of the organic EL device 100 according to an embodiment of the present disclosure is not limited to the above embodiments. The organic EL device 100 according to an embodiment of the present disclosure may have any suitable laminated structure. For example, the organic EL device 100 may exclude at least one of the hole injection layer 130, the hole transfer layer 140, the electron transfer layer 160, or the electron injection layer 170, or may further include another layer. In some embodiments, each layer of the organic EL device 100 may be formed as a single layer or as a plurality of layers.

For example, the organic EL device 100 may further include a hole blocking layer between the electron transfer layer 160 and the emission layer 150 to prevent or reduce the diffusion of triplet excitons and/or holes to the electron transfer layer 160. In some embodiments, the hole blocking layer may include, for example, an oxadiazole derivative, a triazole derivative, and/or a phenanthroline derivative.

EXAMPLES

Hereinafter the monoamine derivative and the organic EL device including the monoamine derivative according to embodiments of the present disclosure will be explained in more detail by referring to examples and comparative examples. The following embodiments are provided only for illustration, and embodiments of the monoamine derivative and the organic EL device are not limited thereto.

Synthesis of Monoamine Derivative

First, a method of synthesizing the monoamine derivative according to an embodiment of the present disclosure will be explained in more detail by referring to the synthetic methods of Compounds 1, 2, 4, 7, 10, and 15. The synthetic methods are described only for illustration, and embodiments of the synthetic method of a monoamine derivative according to an embodiment of the present disclosure are not limited thereto.

1. Synthesis of Compound 1

A monoamine derivative according to an embodiment of the present disclosure, Compound 1, was synthesized by Reactions 1 to 3.

First, Compound B was synthesized by Reaction 1:

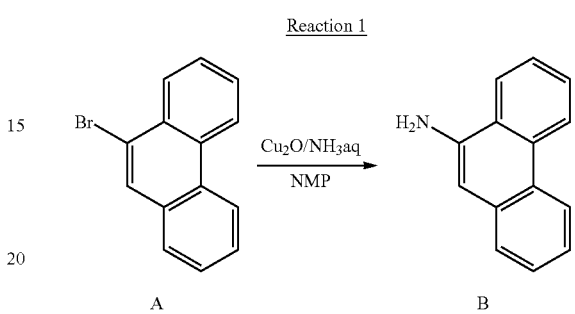

Reaction 1

Under an argon (Ar) atmosphere, Compound A (15.00 g), cuprous oxide ($Cu_2O$, 0.85 g), aqueous ammonia ($NH_{3\ (aq)}$, 20 mL), and N-methyl-pyrrolidone (NMP) (70 mL) were added to a 500 mL, three-necked flask, followed by heating at about 110° C. for about 25 hours. After cooling in the air, water was added, an organic layer was separated, and solvents were removed from the separated organic layer by distillation. The crude product thus obtained was separated by silica gel column chromatography (developing solution: hexane/ethyl acetate) to produce 7.4 g (Yield 66%) of Compound B as a white solid.

The molecular weight of Compound B was measured using fast atom bombardment-mass spectrometry (FAB-MS). The measured value was 193 ($C_{14}H_{11}N$) and was verified to coincide with the calculated value.

Then, Compound C was synthesized by Reaction 2:

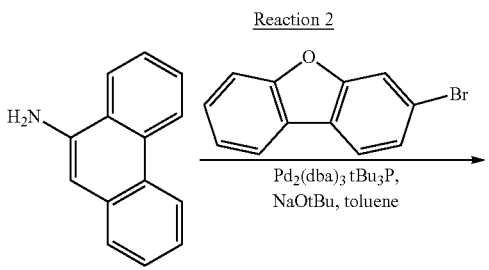

Reaction 2

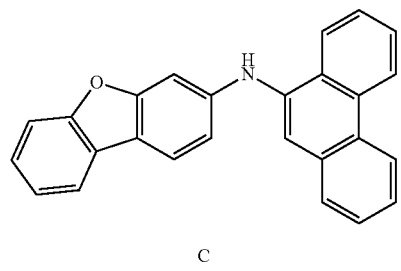

Under an argon (Ar) atmosphere, Compound B (1.00 g), 3-bromo-dibenzofuran (1.41 g), tris(dibenzylideneacetone) palladium(0) ($Pd_2(dba)_3$, 0.27 g), tri-tert-butylphosphine (tBu₃P, 0.084 g), and sodium tert-butoxide (NaOtBu, 1.99 g) were added to a 500 mL, three-necked flask, followed by heating and refluxing in 200 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound C (1.30 g, Yield 70%) as a white solid.

The molecular weight of Compound C was measured using FAB-MS. The measured value was 359 ($C_{26}H_{17}NO$) and was verified to coincide with the calculated value.

Then, Compound 1 was synthesized by Reaction 3:

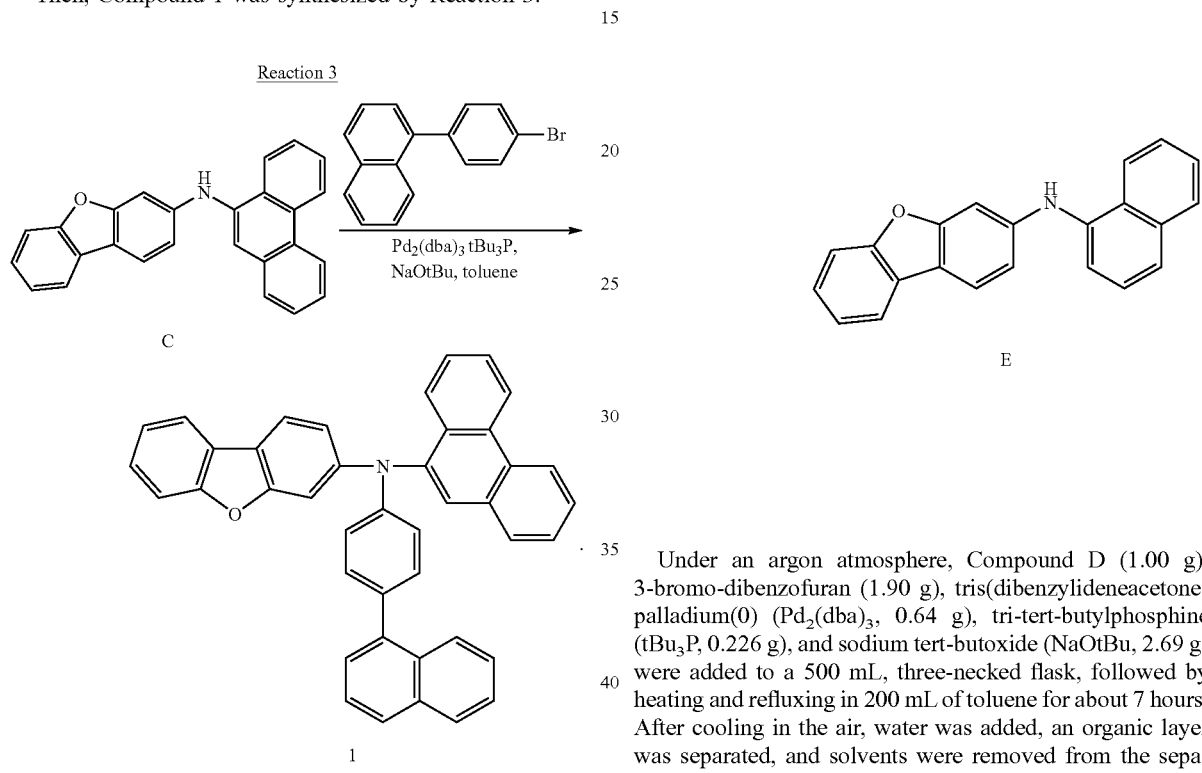

Under an argon atmosphere, Compound C (1.00 g), 1-(4-bromophenyl)naphthalene (0.87 g), tris(dibenzylideneacetone)palladium(0) ($Pd_2(dba)_3$, 0.14 g), tri-tert-butylphosphine (tBu₃P, 0.045 g), and sodium tert-butoxide (NaOtBu, 1.07 g) were added to a 500 mL, three-necked flask, followed by heating and refluxing in 200 mL of a toluene solvent for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound 1 (1.09 g, Yield 70%) as a white solid.

The molecular weight of Compound 1 thus obtained was measured using FAB-MS. The measured value was 561 ($C_{42}H_{27}NO$) and was verified to coincide with the calculated value.

2. Synthesis of Compound 2

A monoamine derivative according to an embodiment of the present disclosure, Compound 2, was synthesized by Reactions 4 and 5.

First, Compound E was synthesized by Reaction 4:

Under an argon atmosphere, Compound D (1.00 g), 3-bromo-dibenzofuran (1.90 g), tris(dibenzylideneacetone)palladium(0) ($Pd_2(dba)_3$, 0.64 g), tri-tert-butylphosphine (tBu₃P, 0.226 g), and sodium tert-butoxide (NaOtBu, 2.69 g) were added to a 500 mL, three-necked flask, followed by heating and refluxing in 200 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound E (1.51 g, Yield 70%) as a white solid.

The molecular weight of Compound E thus obtained was measured using FAB-MS. The measured value was 309 ($C_{22}H_{15}NO$) and was verified to coincide with the calculated value.

Then, Compound 2 was synthesized by Reaction 5:

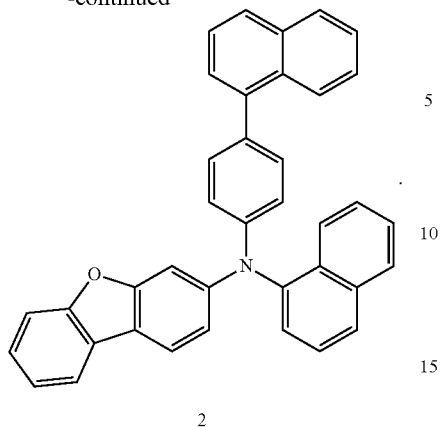

2

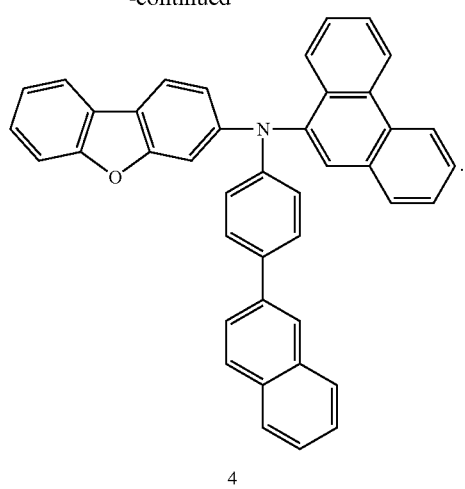

4

Under an argon atmosphere, Compound E (1.00 g), 1-(4-bromophenyl)naphthalene (1.01 g), tris(dibenzylideneacetone)palladium(0) (Pd$_2$(dba)$_3$, 0.30 g), tri-tert-butylphosphine (tBu$_3$P, 0.11 g), and sodium tert-butoxide (NaOtBu, 1.24 g) were added to a 500 mL, three-necked flask, followed by heating and refluxing in 200 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound 2 (1.16 g, Yield 70%) as a white solid.

The molecular weight of Compound 2 thus obtained was measured using FAB-MS. The measured value was 511 (C$_{38}$H$_{25}$NO) and was verified to coincide with the calculated value.

3. Synthesis of Compound 4

A monoamine derivative according to an embodiment of the present disclosure, Compound 4, was synthesized by Reaction 6:

Reaction 6

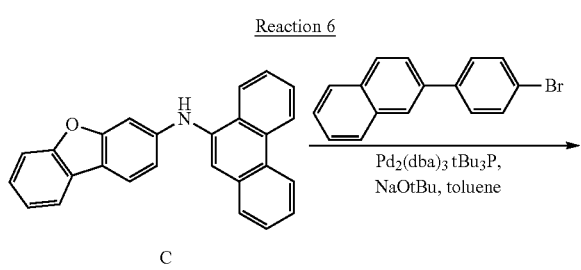

Under an argon atmosphere, Compound C (1.00 g), 2-(4-bromophenyl)naphthalene (0.87 g), tris(dibenzylideneacetone)palladium(0) (Pd$_2$(dba)$_3$, 0.14 g), tri-tert-butylphosphine (tBu$_3$P, 0.045 g), and sodium tert-butoxide (NaOtBu, 1.07 g) were added to a 500 mL, three-necked flask, followed by heating and refluxing in 200 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound 4 (1.01 g, Yield 65%) as a white solid.

The molecular weight of Compound 4 thus obtained was measured using FAB-MS. The measured value was 561 (C$_{42}$H$_{27}$NO) and was verified to coincide with the calculated value.

4. Synthesis of Compound 7

A monoamine derivative according to an embodiment of the present disclosure, Compound 7, was synthesized by Reaction 7:

Reaction 7

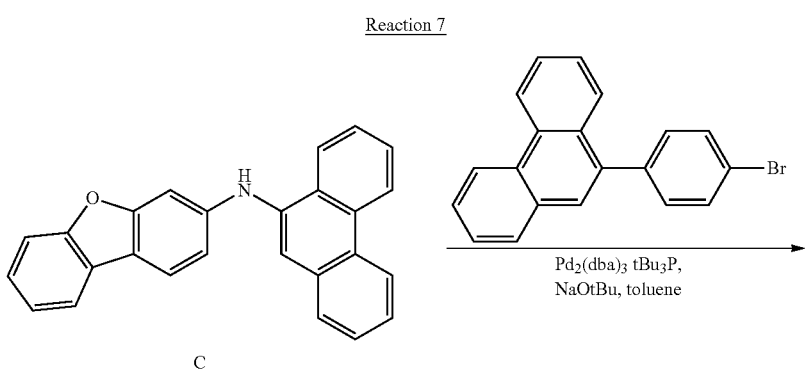

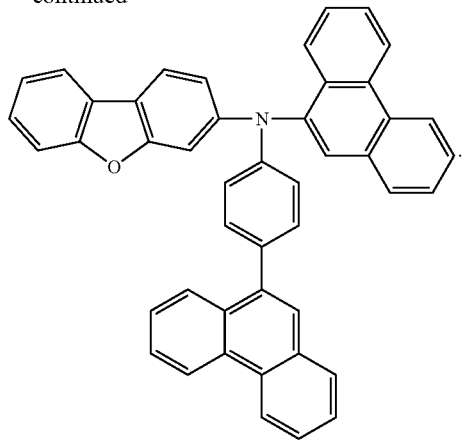

7

Under an argon atmosphere, Compound C (1.00 g), 9-(4-bromophenyl)phenanthrene (1.02 g), tris(dibenzylideneacetone)palladium(0) (Pd$_2$(dba)$_3$, 0.14 g), tri-tert-butylphosphine (tBu$_3$P, 0.045 g), and sodium tert-butoxide (NaOtBu, 1.07 g) were added to a 500 mL, three-necked flask, followed by heating and refluxing in 200 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound 7 (1.19 g, Yield 70%) as a white solid.

The molecular weight of Compound 7 thus obtained was measured using FAB-MS. The measured value was 611 (C$_{46}$H$_{29}$NO) and was verified to coincide with the calculated value.

5. Synthesis of Compound 10

A monoamine derivative according to an embodiment of the present disclosure, Compound 10, was synthesized by Reaction 8:

Reaction 8

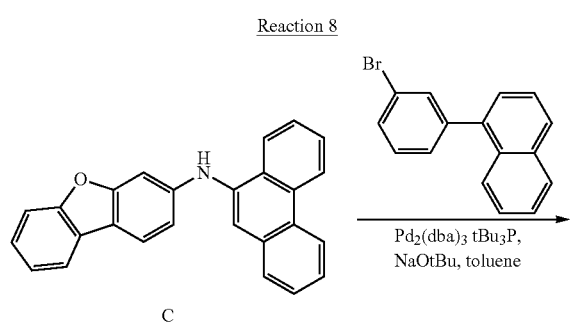

-continued

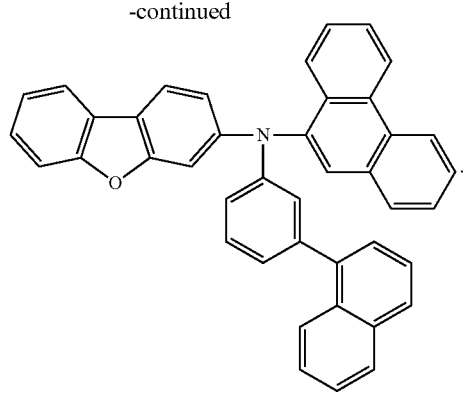

10

Under an argon atmosphere, Compound C (1.00 g), 1-(3-bromophenyl)naphthalene (0.87 g), tris(dibenzylideneacetone)palladium(0) (Pd$_2$(dba)$_3$, 0.14 g), tri-tert-butylphosphine (tBu$_3$P, 0.045 g), and sodium tert-butoxide (NaOtBu, 1.07 g) were added to a 500 mL, three-necked flask, followed by heating and refluxing in 200 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound 10 (1.06 g, Yield 68%) as a white solid.

The molecular weight of Compound 10 thus obtained was measured using FAB-MS. The measured value was 561 (C$_{42}$H$_{27}$NO) and was verified to coincide with the calculated value.

6. Synthesis of Compound 15

A monoamine derivative according to an embodiment of the present disclosure, Compound 15, was synthesized by Reactions 9 and 10.

First, Compound G was synthesized by Reaction 9:

Reaction 9

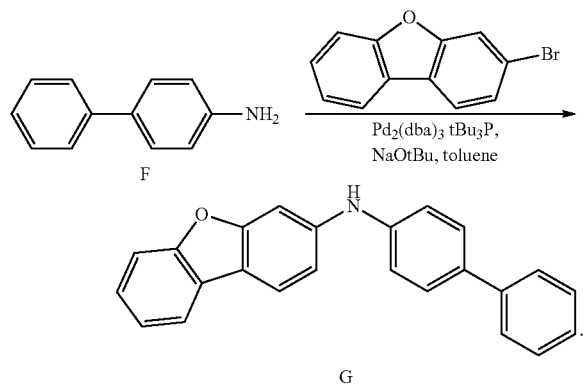

Under an argon atmosphere, Compound F (1.00 g), 3-bromo-dibenzofuran (1.61 g), tris(dibenzylideneacetone)palladium(0) (Pd$_2$(dba)$_3$, 0.54 g), tri-tert-butylphosphine (tBu$_3$P, 0.191 g), and sodium tert-butoxide (NaOtBu, 2.27 g) were added to a 500 mL, three-necked flask, followed by heating and refluxing in 200 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound G (1.47 g, Yield 70%) as a white solid.

The molecular weight of Compound G thus obtained was measured using FAB-MS. The measured value was 337 (C$_{24}$H$_{17}$NO) and was verified to coincide with the calculated value.

Then, Compound 15 was synthesized by Reaction 10:

Under an argon atmosphere, Compound G (1.00 g), 1-(4-bromophenyl)naphthalene (0.93 g), tris(dibenzylideneacetone)palladium(0) (Pd$_2$(dba)$_3$, 0.27 g), tri-tert-butylphosphine (tBu$_3$P, 0.10 g), and sodium tert-butoxide (NaOtBu, 1.15 g) were added to a 500 mL, three-necked flask, followed by heating and refluxing in 200 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound 15 (1.12 g, Yield 70%) as a white solid.

The molecular weight of Compound 15 thus obtained was measured using FAB-MS. The measured value was 537 (C$_{40}$H$_{27}$NO) and was verified to coincide with the calculated value.

Manufacture of Organic EL Device

Then, a blue emitting organic EL device including the monoamine derivative according to an embodiment of the present disclosure was manufactured by the following process using a vacuum deposition method.

Example 1

First, surface treatment using UV-Ozone (O$_3$) was conducted on an ITO-glass substrate patterned and washed in advance. The thickness of the ITO layer (first electrode) in the ITO-glass substrate was about 150 nm. After surface treatment, the glass substrate was inserted into an evaporator for forming organic layers, and a hole injection layer, a hole transfer layer (HTL), an emission layer, and an electron transfer layer were deposited one by one at a vacuum degree of about $10^{-4}$ to about $10^{-5}$ Pa.

The hole injection layer was formed using 4,4',4"-tris(N,N-2-naphthylamino)triphenylamine (2-TNATA) to a layer Reaction 10

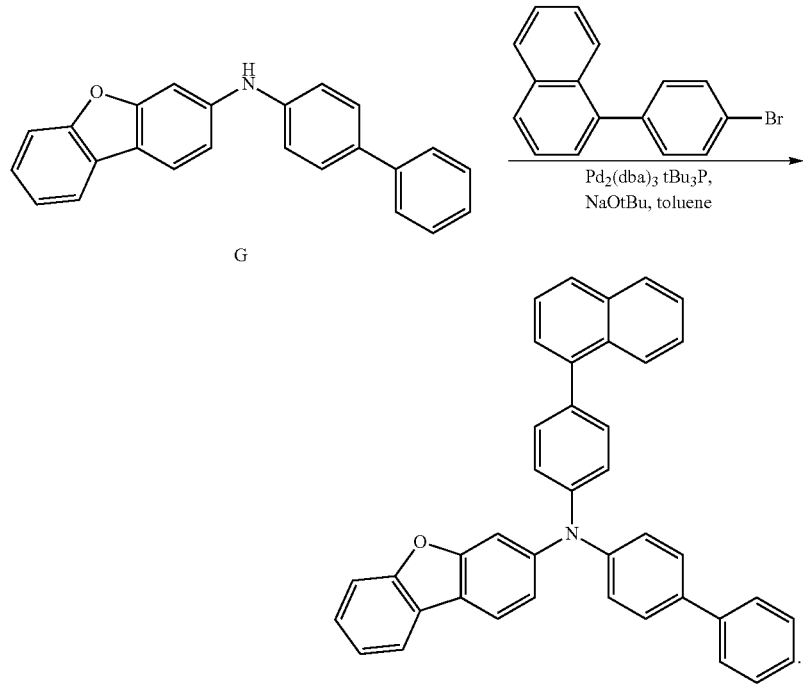

thickness of about 60 nm. The hole transfer layer (HTL) was formed using Compound 1 (synthesized above) to a layer thickness of about 30 nm. The emission layer was formed using 9,10-di(2-naphthyl)anthracene (ADN) as a luminescent host material and 2,5,8,11-tetra-t-butylperylene (TBP) as a dopant material to a layer thickness of about 25 nm. The doping amount of the dopant material was 3 wt % on the basis of the total amount of the host material. The electron transfer layer was formed using $Alq_3$ to a layer thickness of about 25 nm.

Then, the substrate was moved into an evaporator for forming a metal layer, and an electron injection layer and a second electrode were deposited at a vacuum degree of about $10^{-4}$ to about $10^{-5}$ Pa, thereby manufacturing an organic EL device. The electron injection layer was formed using lithium fluoride (LiF) to a layer thickness of about 1 nm, and the second electrode was formed using aluminum (Al) to a layer thickness of about 100 nm. An organic EL device according to Example 1 was thereby manufactured according to the above-described process.

Example 2

An organic EL device according to Example 2 was manufactured by conducting substantially the same procedure described in Example 1, except for forming the hole transfer layer (HTL) using Compound 2.

Example 3

An organic EL device according to Example 3 was manufactured by conducting substantially the same procedure described in Example 1, except for forming the hole transfer layer (HTL) using Compound 4.

Example 4

An organic EL device according to Example 4 was manufactured by conducting substantially the same procedure described in Example 1, except for forming the hole transfer layer (HTL) using Compound 7.

Example 5

An organic EL device according to Example 5 was manufactured by conducting substantially the same procedure described in Example 1, except for forming the hole transfer layer (HTL) using Compound 10.

Example 6

An organic EL device according to Example 6 was manufactured by conducting substantially the same procedure described in Example 1, except for forming the hole transfer layer (HTL) using Compound 15.

Comparative Example 1

An organic EL device according to Comparative Example 1 was manufactured by conducting substantially the same procedure described in Example 1, except for forming the hole transfer layer (HTL) using Compound C1.

Comparative Example 2

An organic EL device according to Comparative Example 2 was manufactured by conducting substantially the same procedure described in Example 1, except for forming the hole transfer layer (HTL) using Compound C2.

Comparative Example 3

An organic EL device according to Comparative Example 3 was manufactured by conducting substantially the same procedure described in Example 1, except for forming the hole transfer layer (HTL) using Compound C3.

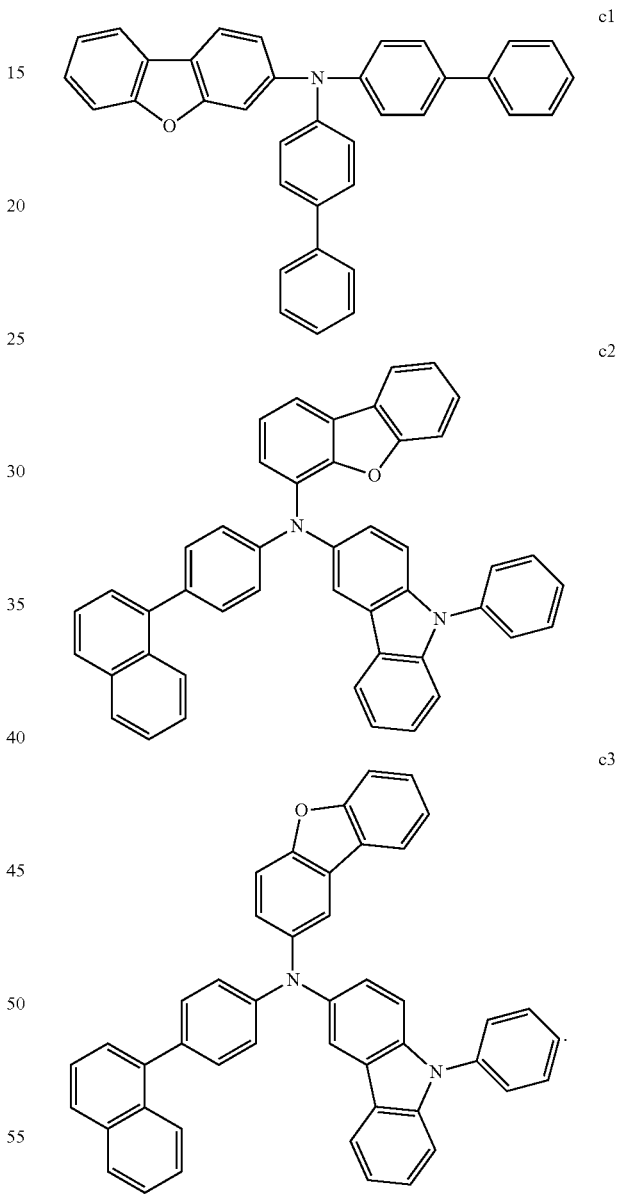

Evaluation Results

The evaluation results of each of the organic EL devices manufactured according to Examples 1 to 6 and Comparative Examples 1 to 3 are shown in Table 1. The emission properties of the organic EL devices thus manufactured were evaluated using a C9920-11 brightness light distribution characteristics measurement system of Hamamatsu Photonics Co. at a current density of 10 mA/cm².

TABLE 1

|  | Hole transfer layer (HTL) | Driving voltage [V] | Emission efficiency [cd/A] |
|---|---|---|---|
| Example 1 | Compound 1 | 6.3 | 7.5 |
| Example 2 | Compound 2 | 6.3 | 7.8 |
| Example 3 | Compound 4 | 6.3 | 7.3 |
| Example 4 | Compound 7 | 6.5 | 7.2 |
| Example 5 | Compound 10 | 6.5 | 7.4 |
| Example 6 | Compound 15 | 6.3 | 7.6 |
| Comparative Example 1 | Comparative Compound C1 | 6.5 | 6.2 |
| Comparative Example 2 | Comparative Compound C2 | 6.7 | 6.5 |
| Comparative Example 3 | Comparative Compound C3 | 6.7 | 6.3 |

Referring to the results of Table 1, the emission efficiencies of the organic EL devices according to Examples 1 to 6, in which hole transfer layers (HTL) were formed using the monoamine derivatives according to embodiments of the present disclosure, were improved compared to those of Comparative Examples 1 to 3.

For example, the emission efficiencies of Examples 1 to 6 were improved compared to that of Comparative Example 1 including Compound C1 in the hole transfer layer (HTL), in which n was 0 and substituent X was a phenyl group with one benzene ring. The emission efficiencies of Examples 1 to 6 were improved compared to those of Comparative Examples 2 and 3, which included Compounds C2 and C3, respectively, in the hole transfer layer (HTL), wherein in each Compound Ar$_2$ was a heteroaryl group.

From the above results, when the monoamine derivative according to an embodiment of the present disclosure has a structure represented by Formula 1, the emission efficiency of the organic EL device including the monoamine derivative may be improved.

In some embodiments, the monoamine derivative according to an embodiment of the present disclosure may be appropriately or suitably used as the material for an organic EL device, and for example, as a hole transfer material. In some embodiments, the monoamine derivative according to an embodiment of the present disclosure may be appropriately or suitably used in an organic EL device that may emit light having a blue to bluish green color.

Hereinafter, the synthetic methods of Compounds 28, 35, and 41, and the experimental results of the organic EL devices including the compounds synthesized will be described in more detail. However, the following embodiments are provided only for illustration, and the scope of the present disclosure is not limited thereto.

Synthesis of Monoamine Derivatives

7. Synthesis of Compound 28

A monoamine derivative according to an embodiment of the present disclosure, Compound 28, was synthesized by Reactions 11 to 13.

First, Compound H was synthesized by Reaction 11:

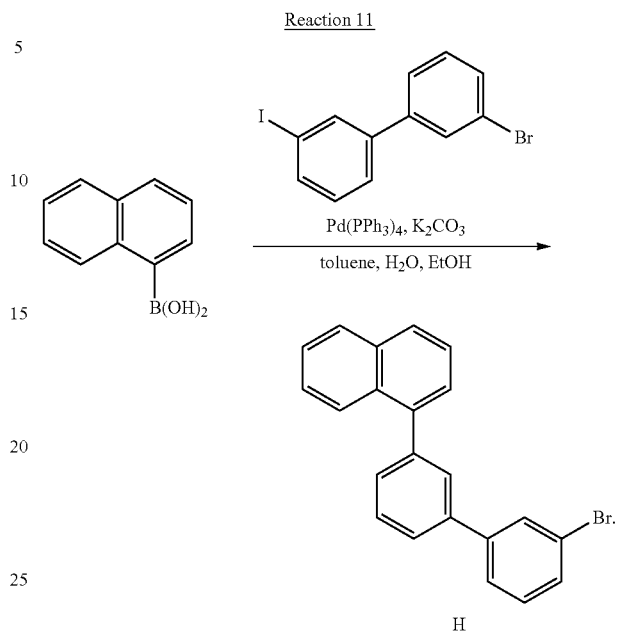

Under an argon atmosphere, 1.00 g of naphthalen-1-ylboronic acid, 2.50 g of 3-bromo-3'-iodo-1,1'-biphenyl, 0.34 g of tetrakis (triphenylphosphine)palladium(0), and 1.15 g of potassium carbonate were added to a 500 mL, three-necked flask, followed by heating and refluxing in 50 mL of toluene, 10 mL of water, and 5 mL of ethanol for about 5 hours. After cooling in the air, water was added to the reactant, an organic layer was separated, and solvents were removed from the separated organic layer by distillation. The crude product thus obtained was separated by silica gel column chromatography (developing solution: toluene/hexane) to produce Compound H (1.46 g, Yield 70%) as a white solid.

The molecular weight of Compound H thus obtained was measured using FAB-MS to be 358 ($C_{22}H_{15}Br$).

Then, Compound I was synthesized by Reaction 12:

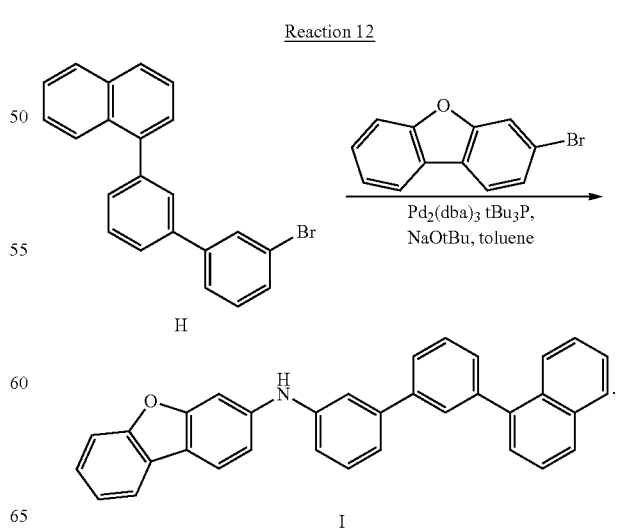

Under an argon atmosphere, 1.00 g of Compound H, 0.46 g of 3-amino dibenzofuran, 0.26 g of bis(dibenzylideneacetone)palladium(0), 0.082 g of tri-tert-butylphosphine, and 0.97 g of sodium tert-butoxide were added to a 500 mL, three-necked flask, followed by heating and refluxing in 200 mL of a toluene solvent for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound I (0.82 g, Yield 70%) as a white solid.

The molecular weight of Compound I thus obtained was measured using FAB-MS to be 461 ($C_{34}H_{23}NO$).

Then, Compound 28 was synthesized by Reaction 13:

Reaction 13

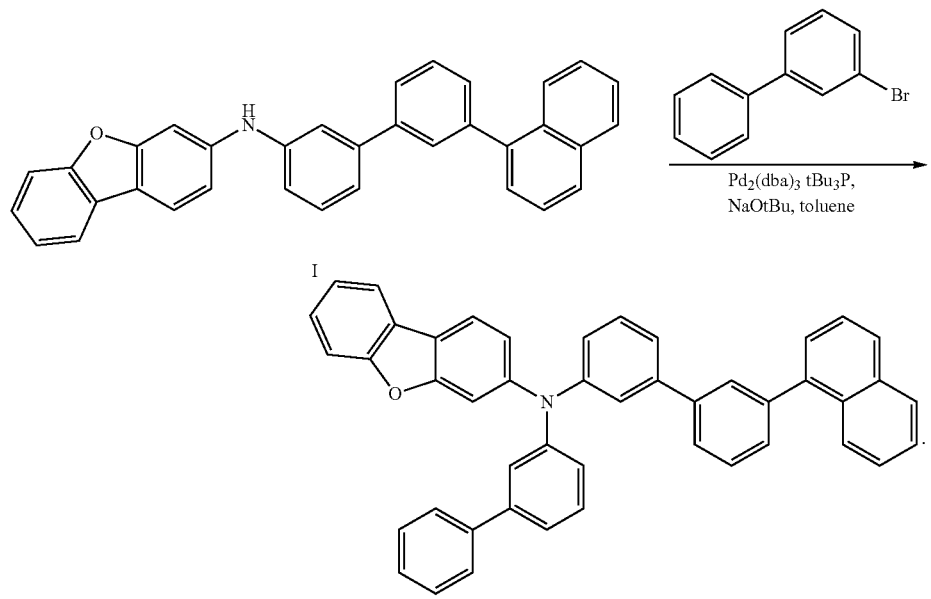

28

Under an argon atmosphere, 1.00 g of Compound I, 0.56 g of 3-bromo-1,1'-biphenyl, 0.22 g of bis(dibenzylideneacetone)palladium(0), 0.07 g of tri-tert-butylphosphine, and 0.83 g of sodium tert-butoxide were added to a 500 mL, three-necked flask, followed by heating and refluxing in 50 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound 28 (0.92 g, Yield 70%) as a white solid.

The molecular weight of Compound 28 thus obtained was measured using FAB-MS to be 613 ($C_{46}H_{31}NO$).

8. Synthesis of Compound 35

A monoamine derivative according to an embodiment of the present disclosure, Compound 25, was synthesized by Reactions 14 to 16.

First, Compound J was synthesized by Reaction 14:

Reaction 14

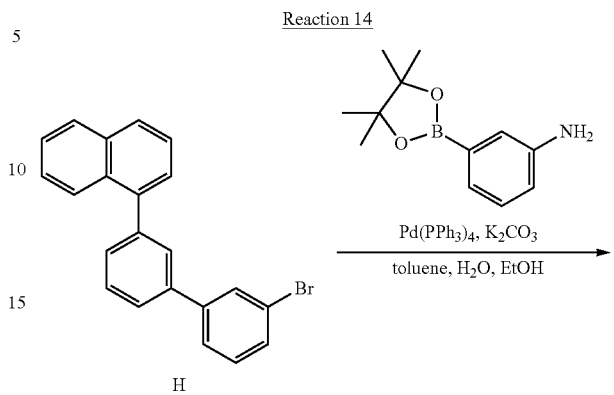

-continued

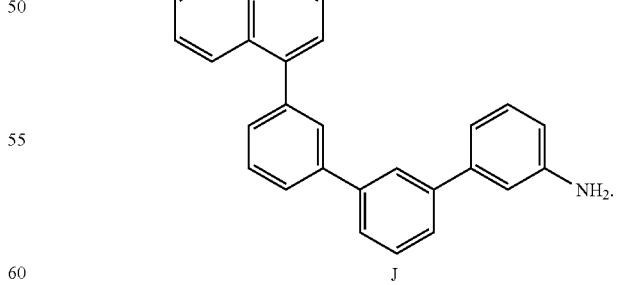

J

Under an argon atmosphere, 1.00 g of Compound H, 0.61 g of 3-(4,4,5,5-tetramethyl-1,3,2-dioxaborolan-2-yl)aniline, 0.16 g of tetrakis (triphenylphosphine)palladium(0), and 0.46 g of potassium carbonate were added to a 500 mL, three-necked flask, followed by heating and refluxing in 30 mL of toluene, 4 mL of water and 2 mL of ethanol for about 5 hours. After cooling in the air, water was added to the reactant, an organic layer was separated, and solvents were removed from the separated organic layer by distillation. The crude product thus obtained was separated by silica gel column chromatography (developing solution: toluene/hexane) to produce Compound J (0.72 g, Yield 70%) as a white solid.

The molecular weight of Compound J thus obtained was measured using FAB-MS to be 371 ($C_{28}H_{21}N$).

Then, Compound K was synthesized by Reaction 15.

Reaction 15

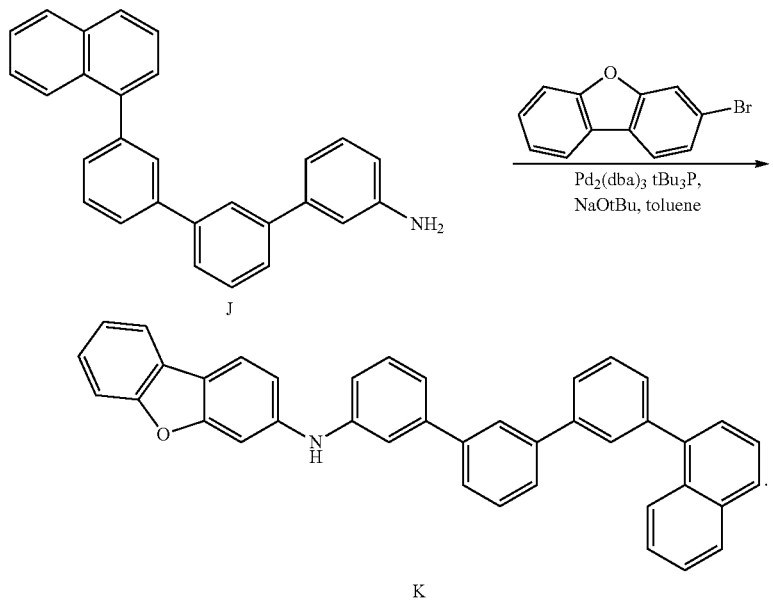

Under an argon atmosphere, 1.00 g of Compound J, 0.73 g of 3-bromo dibenzofuran, 0.28 g of bis(dibenzylideneacetone)palladium(0), 0.09 g of tri-tert-butylphosphine, and 1.04 g of sodium tert-butoxide were added to a 500 mL, three-necked flask, followed by heating and refluxing in 50 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound K (0.98 g, Yield 70%) as a white solid.

The molecular weight of Compound K thus obtained was measured using FAB-MS and was 537 ($C_{40}H_{27}NO$).

Then, Compound 35 was synthesized by Reaction 16:

Reaction 16

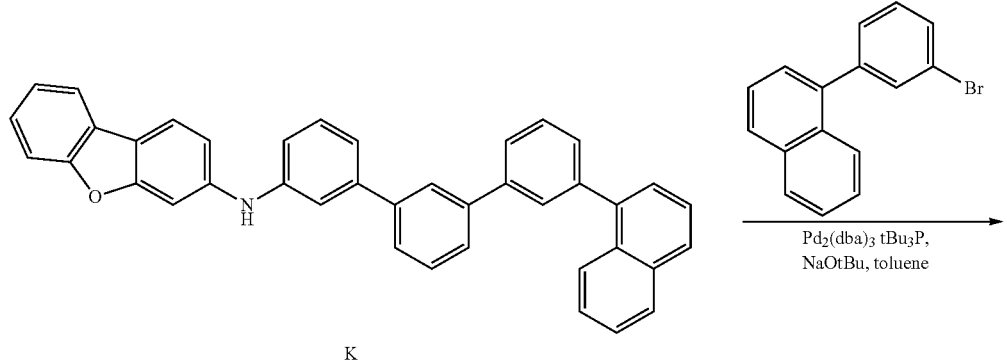

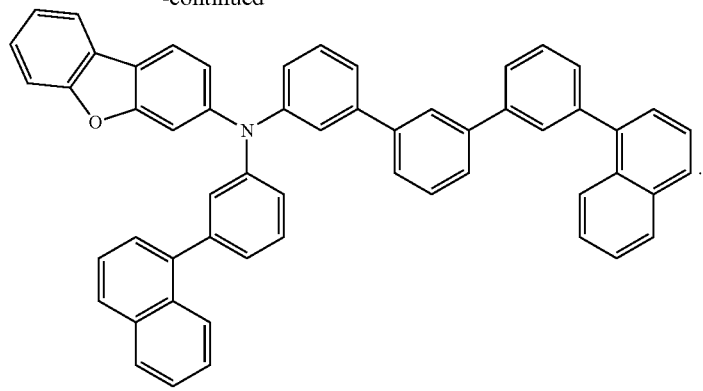

35

Under an argon atmosphere, 1.00 g of Compound K, 0.58 g of 1-(3-bromophenyl)naphthalene, 0.19 g of bis(dibenzylideneacetone)palladium(0), 0.06 g of tri-tert-butylphosphine, and 0.72 g of sodium tert-butoxide were added to a 500 mL, three-necked flask, followed by heating and refluxing in 40 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound 35 (0.93 g, Yield 70%) as a white solid.

The molecular weight of Compound 35 thus obtained was measured using FAB-MS to be 739 ($C_{56}H_{37}NO$).

9. Synthesis of Compound 41

A monoamine derivative according to an embodiment of the present disclosure, Compound 41, was synthesized by Reactions 17 to 19.

First, Compound M was synthesized by Reaction 17:

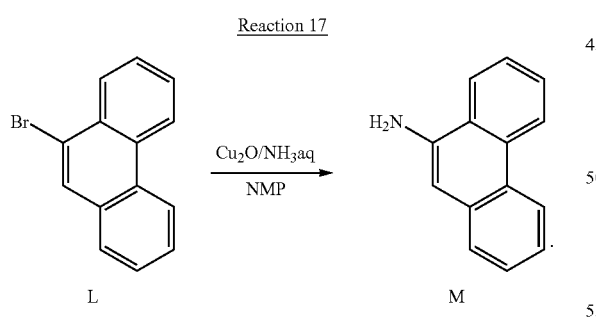

Under an argon atmosphere, 15.00 g of Compound L, 0.85 g of cuprous oxide, 20 mL of aqueous ammonia, and 70 mL of NMP were added to a 500 mL, three-necked flask, followed by heating and refluxing at 110° C. for about 25 hours. After cooling in the air, water was added to the reactant, an organic layer was separated, and solvents were removed from the separated organic layer by distillation. The crude product thus obtained was separated by silica gel column chromatography (developing solution: toluene/hexane) to produce Compound M (7.4 g, Yield 66%) as a white solid.

The molecular weight of Compound M thus obtained was measured using FAB-MS to be 193 ($C_{14}H_{11}N$).

Then, Compound N was synthesized by Reaction 18:

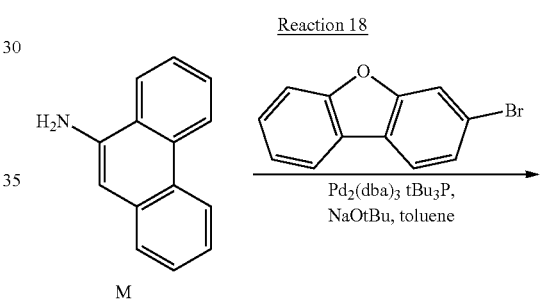

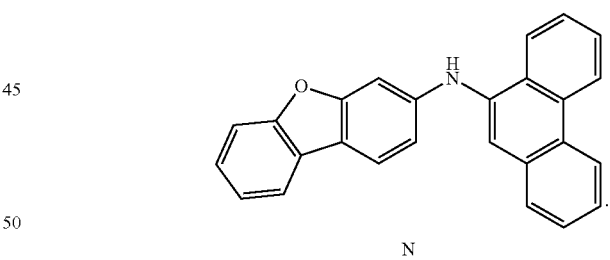

Under an argon atmosphere, 1.00 g of Compound M, 1.41 g of 3-bromo dibenzofuran, 0.27 g of bis(dibenzylideneacetone)palladium(0), 0.084 g of tri-tert-butylphosphine, and 1.99 g of sodium tert-butoxide were added to a 500 mL, three-necked flask, followed by heating and refluxing in 200 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound N (1.30 g, Yield 70%) as a white solid.

The molecular weight of Compound N thus obtained was measured using FAB-MS to be 359 ($C_{26}H_{17}NO$).

Then, Compound 41 was synthesized by Reaction 19:

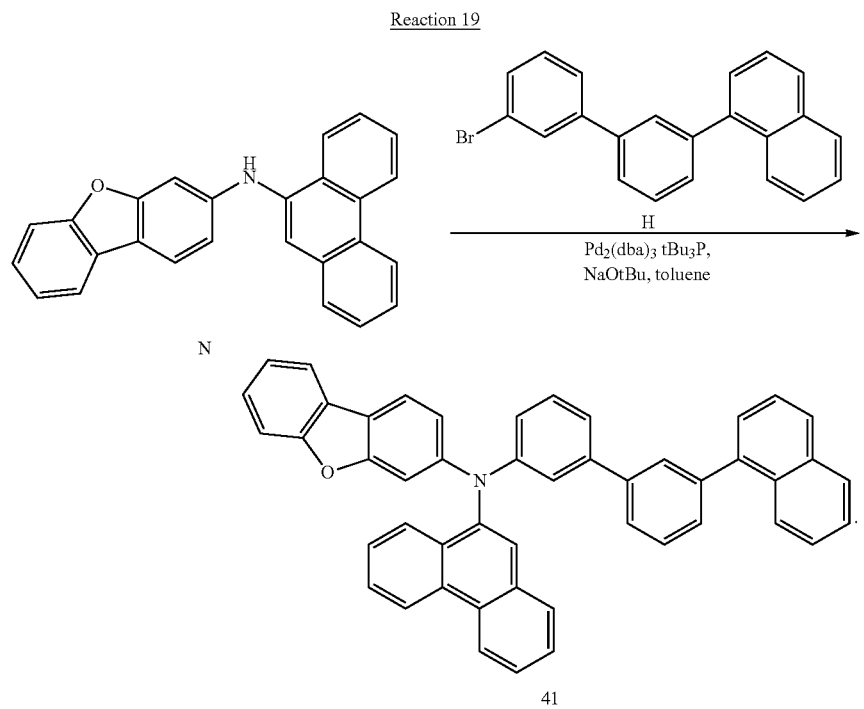

Under an argon atmosphere, 1.00 g of Compound N, 1.10 g of Compound H, 0.29 g of bis(dibenzylideneacetone)palladium(0), 0.09 g of tri-tert-butylphosphine, and 1.07 g of sodium tert-butoxide were added to a 500 mL, three-necked flask, followed by heating and refluxing in 60 mL of toluene for about 7 hours. After cooling in the air, water was added, an organic layer was separated, and solvents were removed from the separated organic layer by distillation. The crude product thus obtained was separated by silica gel column chromatography (developing solution: toluene/hexane) to produce Compound 41 (1.24 g, Yield 70%) as a white solid.

The molecular weight of Compound 41 thus obtained was measured using FAB-MS to be 637 ($C_{48}H_{31}NO$).

Manufacture of Organic EL Device

Example 7

An organic EL device according to Example 7 was manufactured by conducting substantially the same procedure described in Example 1, except for forming the hole transfer layer (HTL) using Compound 28.

Example 8

An organic EL device according to Example 8 was manufactured by conducting substantially the same procedure described in Example 1, except for forming the hole transfer layer (HTL) using Compound 35.

Example 9

An organic EL device according to Example 9 was manufactured by conducting substantially the same procedure described in Example 1, except for forming the hole transfer layer (HTL) using Compound 41.

Comparative Example 4

An organic EL device according to Comparative Example 4 was manufactured by conducting substantially the same procedure described in Example 1, except for forming the hole transfer layer (HTL) using Compound C4.

Comparative Example 5

An organic EL device according to Comparative Example 5 was manufactured by conducting substantially the same procedure described in Example 1, except for forming the hole transfer layer (HTL) using Compound C5.

Comparative Example 6

An organic EL device according to Comparative Example 6 was manufactured by conducting substantially the same procedure described in Example 1, except for forming the hole transfer layer (HTL) using Compound C6.

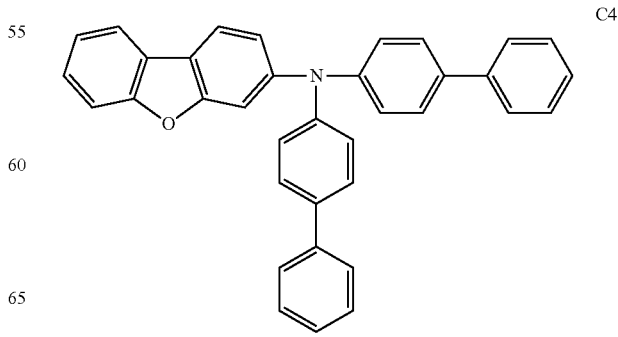

-continued

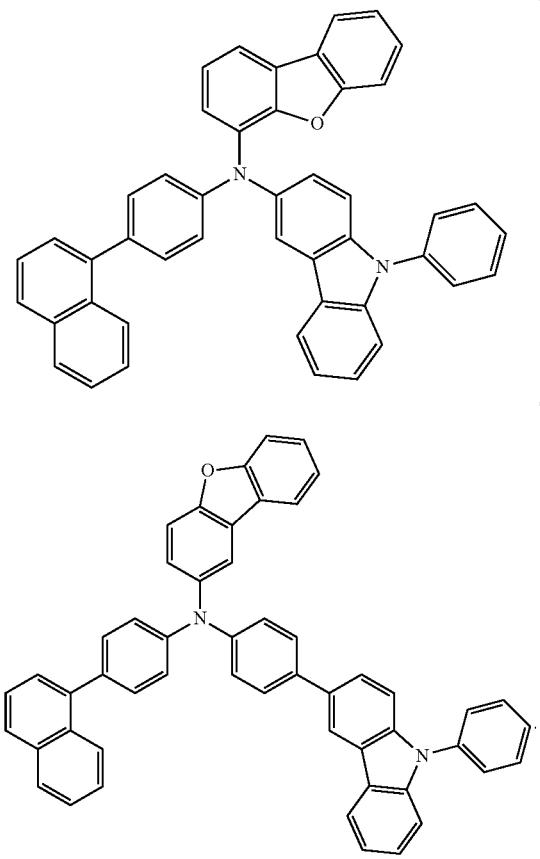

C5

C6

Evaluation Results

The evaluation results of each of the organic EL devices manufactured according to Examples 7 to 9 and Comparative Examples 4 to 6 are shown in the following Table 2. The emission properties of the organic EL devices thus manufactured were evaluated using a C9920-11 brightness light distribution characteristics measurement system by Hamamatsu Photonics Co. at a current density of 10 mA/cm$^2$.

TABLE 2

|  | Hole transfer layer (HTL) | Voltage [V] | Emission efficiency [cd/A] |
| --- | --- | --- | --- |
| Example 7 | Compound 28 | 6.3 | 7.8 |
| Example 8 | Compound 35 | 6.3 | 7.5 |
| Example 9 | Compound 41 | 6.5 | 7.2 |
| Comparative Example 4 | Comparative Compound C4 | 6.5 | 6.2 |
| Comparative Example 5 | Comparative Compound C5 | 6.7 | 6.5 |
| Comparative Example 6 | Comparative Compound C6 | 6.7 | 6.3 |

Referring to the results of Table 2, the driving voltage was decreased and the emission efficiency was improved in each of the organic EL devices in which hole transfer layers (HTL) were formed using the monoamine derivatives (e.g., according to Examples 7 to 9), compared to those according to Comparative Examples 4 to 6.

For example, the driving voltage was decreased and the emission efficiency was improved in each of the organic EL devices according to Examples 7 to 9 using Compounds 28, 35, and 41, respectively, in which a phenylene group directly connected to a nitrogen atom (N) was substituted at a meta position, compared to the organic EL devices according to Comparative Examples 4 to 6 using Comparative Compounds C4 to C6, in each of which a phenylene group directly connected to a nitrogen atom (N) was substituted at the para position.

The driving voltage was decreased and the emission efficiency was improved in each of the organic EL devices according to Examples 7 to 9 using Compounds 28, 35, and 41, respectively, in which an amine group is connected at position 3 of dibenzofuran, compared to those according to Comparative Example 5 using Comparative Compound C5, in which an amine group is connected at position 4 of dibenzofuran, or Comparative Example 6 using Comparative Compound C6, in which an amine group is connected at position 2 of dibenzofuran.

As described above, according to an embodiment of the present disclosure, the emission efficiency of an organic EL device may be further improved.

As used herein, expressions such as "at least one of", "one of", and "selected from", when preceding a list of elements, modify the entire list of elements and do not modify the individual elements of the list. Further, the use of "may" when describing embodiments of the present disclosure refers to "one or more embodiments of the present disclosure".

In addition, as used herein, the terms "use", "using", and "used" may be considered synonymous with the terms "utilize", "utilizing", and "utilized", respectively.

As used herein, the terms "substantially", "about", and similar terms are used as terms of approximation and not as terms of degree, and are intended to account for the inherent deviations in measured or calculated values that would be recognized by those of ordinary skill in the art.

Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

While one or more example embodiments of the present disclosure have been described with reference to the drawing, it will be understood that the present disclosure should not be limited to these example embodiments, but various changes and modifications can be made by one of ordinary skill in the art within the spirit and scope of the present disclosure as defined by the following claims and equivalents thereof.

What is claimed is:
1. An organic electroluminescent (EL) device, comprising:
   a first electrode;
   a second electrode on the first electrode; and
   at least one organic layer between the first electrode and the second electrode, wherein the at least one organic layer comprises a monoamine derivative having only one amine group, represented by Formula 1:

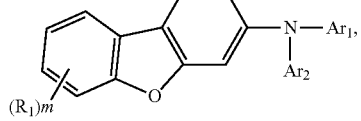

Formula 1 wherein in Formula 1,

Ar₁ is represented by Formula 2,

Ar₂ is an unsubstituted phenyl group, biphenyl group, terphenyl group, naphthyl group, anthryl group, phenanthrenyl group, fluorenyl group, indenyl group, pyrenyl group, fluoranthenyl group, or triphenylenyl group; or a 9,9-disubstituted fluorenyl group, Ar₁ and Ar₂ are different from each other, m is an integer from 0 to 4, R₁ is a substituted or unsubstituted aryl group having 6 to 30 carbon atoms for forming a ring, and when m is 2 or more, a plurality of R₁ may combine to form a ring,

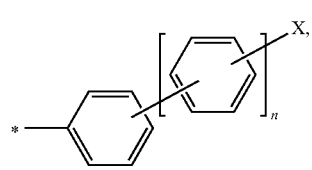

Formula 2 wherein in Formula 2, n is 0, and X is represented by one of the following groups:

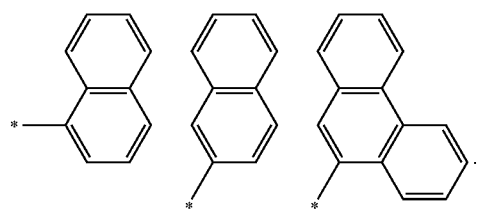

wherein the at least one organic layer comprising the monoamine derivative is a hole transfer layer.

2. The organic EL device of claim 1, wherein m is 0.

3. The organic EL device of claim 1, wherein Ar₂ is an unsubstituted aryl group having 6 to 14 carbon atoms for forming a ring.

4. The organic EL device of claim 1, wherein the monoamine derivative represented by Formula 1 is represented by at least one selected from the following Compounds 1 to 18:

1

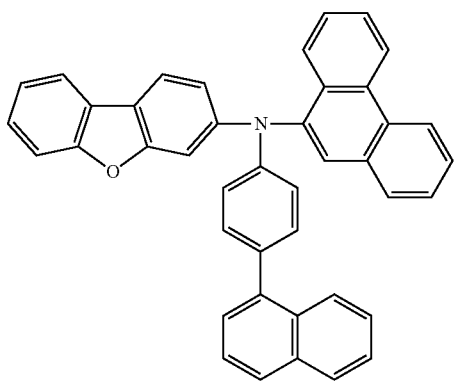

2

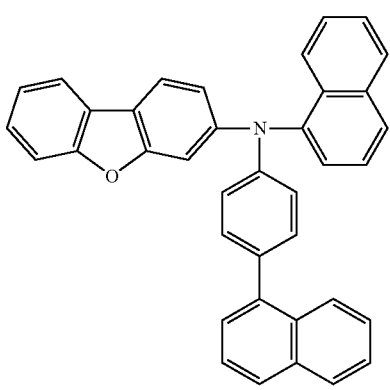

3

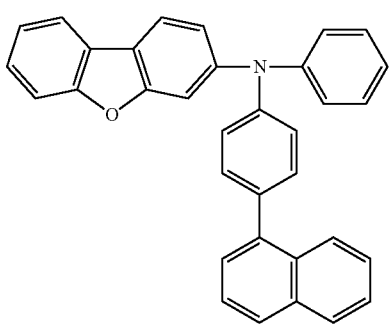

4

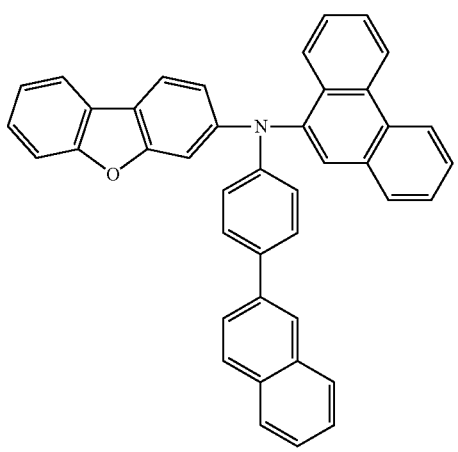

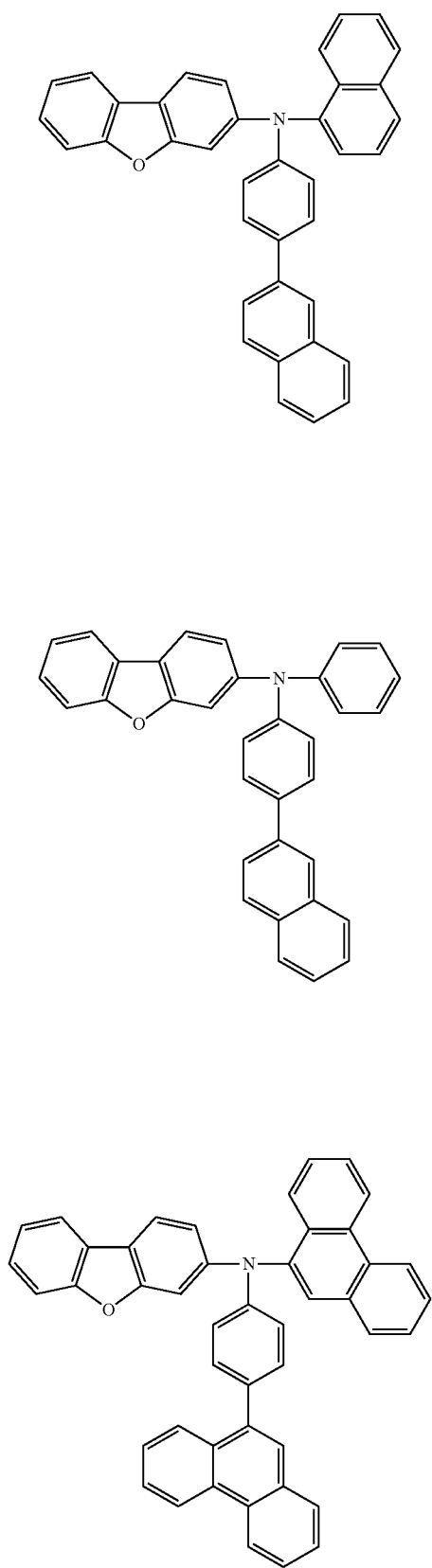
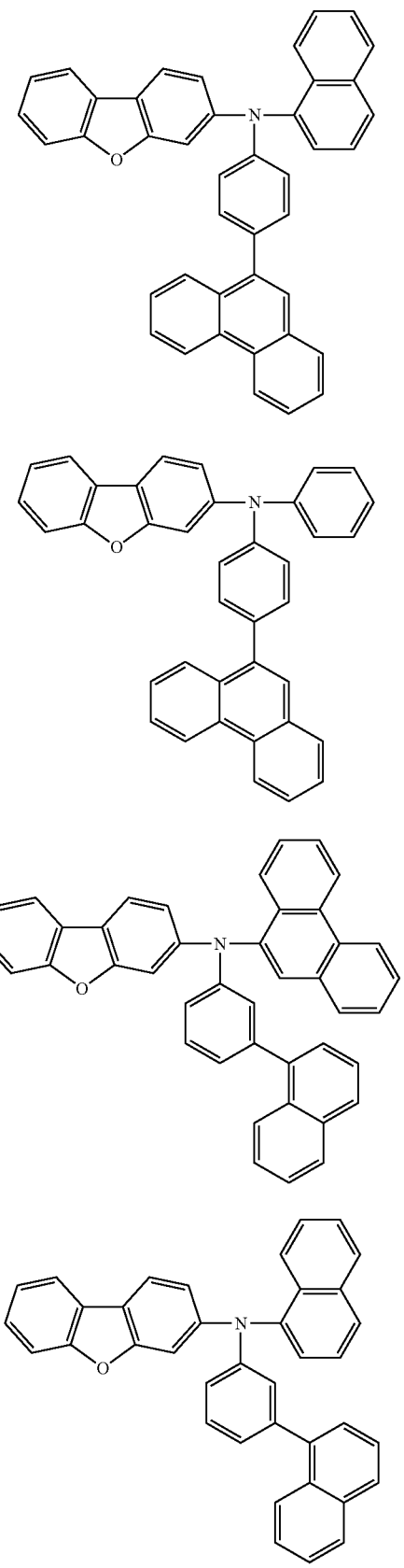

12
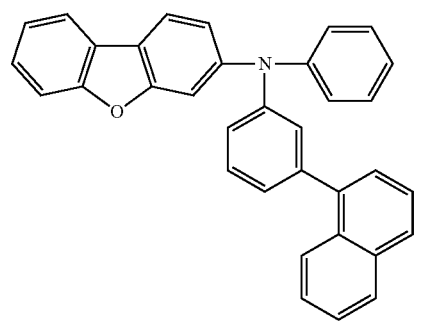
13
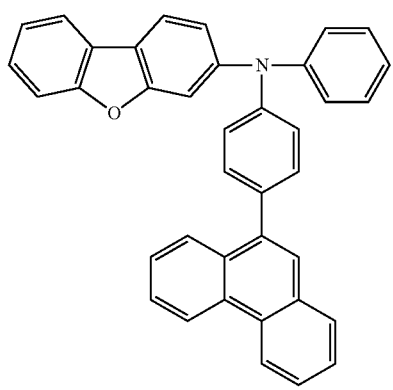
14
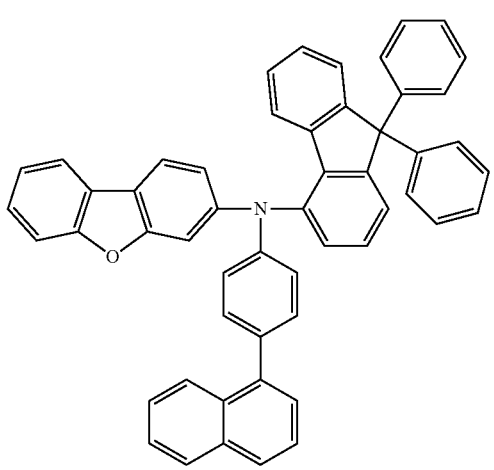
15
16
17
18
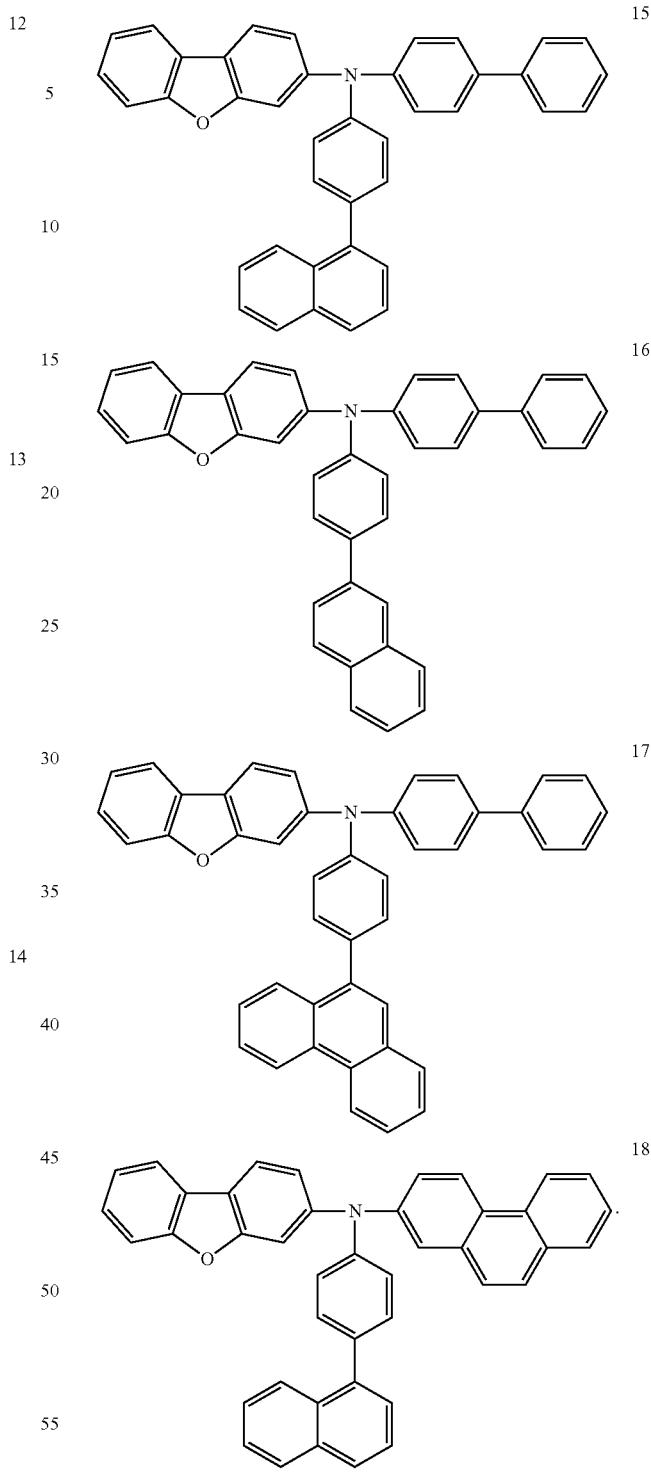
* * * * *